US009550981B2

(12) United States Patent
Chin et al.

(10) Patent No.: US 9,550,981 B2
(45) Date of Patent: Jan. 24, 2017

(54) MODIFIED TAFAZZIN PROTEINS AND METHODS OF MAKING AND USING THE SAME

(71) Applicant: University of Washington Center for Commercialization, Seattle, WA (US)

(72) Inventors: Michael T. Chin, Seattle, WA (US); Wei-Ming Chien, Seattle, WA (US); Ana Dinca, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/603,141

(22) Filed: Jan. 22, 2015

(65) Prior Publication Data

US 2015/0203827 A1 Jul. 23, 2015

Related U.S. Application Data

(60) Provisional application No. 61/930,264, filed on Jan. 22, 2014.

(51) Int. Cl.
*A61K 38/00* (2006.01)
*C12N 9/10* (2006.01)
*C07K 14/005* (2006.01)

(52) U.S. Cl.
CPC ............ *C12N 9/1029* (2013.01); *C07K 14/005* (2013.01); *A61K 38/00* (2013.01); *C07K 2319/10* (2013.01); *C12Y 203/01023* (2013.01)

(58) Field of Classification Search
None
See application file for complete search history.

(56) References Cited

U.S. PATENT DOCUMENTS

| | | | |
|---|---|---|---|
| 9,249,184 B2 | 2/2016 | Robbins et al. | |
| 2002/0103121 A1 | 8/2002 | La Thangue et al. | |
| 2002/0151004 A1* | 10/2002 | Craig | A61K 9/5068 435/173.1 |
| 2003/0060399 A1 | 3/2003 | Brophy et al. | |
| 2004/0121942 A1 | 6/2004 | Chien et al. | |
| 2006/0251641 A1 | 11/2006 | Keimel | |
| 2007/0135335 A1* | 6/2007 | Collier | C12N 9/1205 514/4.8 |
| 2011/0177051 A1 | 7/2011 | Galski-Lorberboum et al. | |
| 2012/0244136 A1 | 9/2012 | Robbins et al. | |
| 2014/0100128 A1 | 4/2014 | Narain et al. | |
| 2014/0377243 A1* | 12/2014 | Chung | C07K 14/51 424/94.3 |

FOREIGN PATENT DOCUMENTS

| | | |
|---|---|---|
| WO | 2010/017515 | 2/2010 |
| WO | WO2012165737 A1 * | 6/2012 |
| WO | 2014/134554 | 9/2014 |

OTHER PUBLICATIONS

Sawat et al. Eur. J. Nanomed. 2013; 5(3): 141-158.*
Chin, M.T., "Tafazzin enzyme replacement therapy for heart muscle in Barth syndrome," Abstract only, accessed online at: https://www.barthsyndrome.org/view.asp?ccid=396, 1 page, (retrieved Jan. 5, 2015).
Schlame, et al., "The mechanism of acyl specific phospholipid remodeling by tafazzin," Nature Chemical Biology, vol. 8, No. 10, pp. 862-869, (Jul. 2, 2012).
Xu, et al., "Characterization of Tafazzin Splice Variants from Humans and Fruit Flies," The Journal of Biological Chemistry, vol. 284, No. 42, pp. 29230-29239, (Oct. 16, 2009).
Schlame, et al., "Cardiolipin remodeling and the function of tafazzin," Biochimica et Biophysica Acta, vol. 1831, pp. 582-588, (Nov. 28, 2012).
Thorén, et al., "The Antennapedia peptide penetratin translocates across lipid bilayers—the first direct observation," Federation of European Biochemical Societies Letters, vol. 482, pp. 265-268, (2000).
Bione, et al., "A novel X-linked gene, G4.5. is responsible for Barth syndrome," Nature Genetics, vol. 12, pp. 385-389, (Apr. 1996).
Barth, et al., "An X-Linked Mitochondrial Disease Affecting Cardiac Muscle, Skeletal Muscle and Neutrophil Leucocytes," Journal of the Neurological Sciences, vol. 62, pp. 327-355, (1983).
Pu, W.T., "Modeling Barth Syndrome using Patient-Specific, iPSC-derived Cardiomyocytes," presented at Jun. 2012 Barth Syndrome Foundation International Conf., 73 pages, (2012).
Rapoport, et al., "Successful TAT-mediated enzyme replacement therapy in a mouse model of mitochondrial E3 deficiency," J. Mol. Med., vol. 89, pp. 161-170, (Nov. 16, 2010).
Brandner, et al., "Taz1, an Outer Mitochondrial Membrane Protein, Affects Stability and Assembly of Inner Membrane Protein Complexes: Implications for Barth Syndrome," Molecular Biology of the Cell, vol. 16, No. 11, pp. 5202-5214, (Nov. 2005).
Bleyl, et al., "Xq28-linked Noncompaction of the Left Ventricular Myocardium: Prenatal Diagnosis and Pathologic Analysis of Affected Individuals," American Journal of Medical Genetics, vol. 72, No. 3, pp. 257-265, (1997).
Barth, et al., "X-linked cardioskeletal myopathy and neutropenia (Barth syndrome): Respiratory-chain abnormalities in cultured fibroblasts," Journal of Inherited Metabolic Disease, vol. 19, No. 2, pp. 157-160, (1996).

(Continued)

*Primary Examiner* — Jeanette Lieb
(74) *Attorney, Agent, or Firm* — Stoel Rives LLP; Zhi-Xiang (Alex) Oh

(57) ABSTRACT

Fusion proteins comprising a tafazzin peptide and a cellular permeability peptide are disclosed. The tafazzin peptide may be coupled to the permeability peptide through a polypeptide linker. Methods of making and using the fusion proteins are also disclosed. For example, the disclosed fusion proteins may be used to treat a patient having a disorder associated with a tafazzin deficiency or a remodeled cardiolipin deficiency (e.g., Barth syndrome). Additionally, the disclosed fusion proteins may be used in prophylaxis against developing a disorder associated with a tafazzin deficiency or a remodeled cardiolipin deficiency in a patient at risk of developing such a disorder.

30 Claims, 17 Drawing Sheets

(56) References Cited

OTHER PUBLICATIONS

Valianpour, et al., "Linoleic acid supplementation of Barth syndrome fibroblasts restores cardiolipin levels: implications for treatment," Journal of Lipid Research, vol. 44, No. 3, pp. 560-566, (Dec. 16, 2002).

Valianpour, et al., "Cardiolipin deficiency in X-linked cardioskeletal myopathy and neutropenia (Barth syndrome, MIM 302060): A study in cultured skin fibroblasts," The Journal of Pediatrics, vol. 141, No. 5, pp. 729-733, (Nov. 2002).

Schlame, et al., "Deficiency of Tetralinoleoyl-Cardiolipin in Barth Syndrome," Annals of Neurology, vol. 51, No. 5, pp. 634-637, (2002).

Vaz, et al., "Only One Splice Variant of the Human TAZ Gene Encodes a Functional Protein With a Role in Cardiolipin Metabolism," The Journal of Biological Chemistry, vol. 278, No. 44, pp. 43089-43094, (Jun. 5, 2003).

He, Q., "Tafazzin knockdown causes hypertrophy of neonatal ventricular myocytes," American Journal of Physiology Heart and Circulatory Physiology, vol. 299, No. 1, pp. H210-H216, (Mar. 26, 2010).

Frankel, et al., "Cellular Uptake of the Tat Protein from Human Immunodeficiency Virus," Cell, vol. 55, No. 6, pp. 1189-1193, (Dec. 23, 1988).

Min, et al., "Gene delivery using a derivative of the protein transduction domain peptide, K-Antp.," Biomaterials, vol. 31, No. 7, pp. 1858-1864, (2010).

Houtkooper, et al., "Identification and characterization of human cardiolipin synthase," Federation of European Biochemical Societies Letters, vol. 580, No. 13, pp. 3059-3064, (2006).

Kulik, et al., "Bloodspot Assay Using HPLC-tandem Mass Spectrometry for Detection of Barth Syndrome," Clinical Chemistry, vol. 54, No. 2, pp. 371-378, (2008).

Saks, et al., "Permeabilized cell and skinned fiber techniques in studies of mitochondrial function in vivo," Molecular Cell Biochemistry, vol. 184, pp. 81-100, (1998).

Sambrano, et al., "Navigating the signaling network in mouse cardiac myocytes," Nature, vol. 420, pp. 712-714, (Dec. 12, 2002).

Lindegger, et al., "Paradoxical SR $Ca^{2+}$ release in guinea-pig cardiac myocytes after β-adrenergic stimulation revealed by two-photon photolysis of caged $Ca^{2+}$," J. Physiol., vol. 565 (Pt 3), pp. 801-813, (Mar. 17, 2005).

Zhu, et al., "Local Control of Excitation-Contraction Coupling in Human Embryonic Stem Cell-Derived Cardiomyocytes," PLoS One, vol. 4, No. 4, e5407, 11 pages, (Apr. 2009).

Muzumdar, et al., "A Global Double-Fluorescent Cre Reporter Mouse," Genesis, vol. 45, pp. 593-605, (2007).

Mao, et al., "Improved reporter strain for monitoring Cre recombinase-mediated DNA excisions in mice," Proc. Natl. Acad. Sci. USA, vol. 96, pp. 5037-5042, (Apr. 1999).

Zhou, et al., "Inducible and Reversible Transgene Expression in Human Stem Cells After Efficient and Stable Gene Transfer," Stem Cells, vol. 25, pp. 779-789, (2007).

Oishi, et al., "Myo-mechanical Analysis of Isolated Skeletal Muscle," video article, Journal of Visualized Experiments, 5 pages, (2011).

Stone, et al., "Dose- and Volume Dependent-Response to Intramuscular Injection of Botulinum Neurotoxin-A Optimizes Muscle Force Decrement in Mice," Journal of Orthopaedic Research, vol. 29, pp. 1764-1770, (Apr. 13, 2011).

McCullagh, et al., "Analysis of skeletal muscle function in the C57BL6/SVI29 syncoilin knockout mouse," Mammalian Genome, vol. 19, pp. 339-351, (Jul. 2, 2008).

Bekeredjian, et al., "Augmentation of Cardiac Protein Delivery Using Ultrasound Targeted Microbubble Destruction," Ultrasound in Medicine & Biology, vol. 31, No. 5, pp. 687-691, (2005).

Geis, et al., "Spatial Distribution of Ultrasound Targeted Microbubble Destruction Increases Cardiac Transgene Expression But Not Capillary Permeability," Ultrasound in Medicine & Biology, vol. 35, No. 7, pp. 1119-1126, (2009).

Acehan, et al., "Distinct effects of tafazzin deletion in differentiated and undifferentiated mitochondria," Mitochondrion, vol. 9, pp. 86-95, (2009).

Dudek, et al., "Cardiolipin deficiency affects respiratory chain function and organization in an induced pluripotent stem cell model of Barth syndrome," Stem Cell Research, vol. 11, pp. 806-819, (May 28, 2013).

He, et al., "Tafazzin knockdown interrupts cell cycle progression in cultured neonatal ventricular fibroblasts," Am. J. Physiol. Heart Circ. Physiol., vol. 305, pp. H1332-H1343, (Aug. 30, 2013).

Khuchua, Z., "Impaired fatty-acid metabolism in tafazzin-deficient mice," presented at Jun. 2012 Barth Syndrome Foundation 6th International Scientific, Medical & Family Conference, 26 pages, (Jun. 25-30, 2012).

Xu, et al., "The enzymatic function of tafazzin," The Journal of Biological Chemistry, vol. 281, No. 51, pp. 39217-39224, (Dec. 22, 2006).

Wang et al., "Modeling the mitochondrial cardiomyopathy of Barth syndrome with induced pluripotent stem cell and heart-on-chip technologies," Nature Medicine, vol. 20, No. 6, pp. 616-623, (Jun. 2014).

Sparagna, et al., "Loss of cardiac tetralinoleoyl cardiolipin in human and experimental heart failure," Journal of Lipid Research, vol. 48, No. 7, pp. 1559-1570, (Apr. 10, 2007).

Aprikyan, et al., "Advances in the understanding of Barth syndrome," British Journal of Haematology, vol. 161, No. 3, pp. 330-338, (Feb. 25, 2013).

Khuchua, et al., "A Zebrafish Model of Human Barth Syndrome Reveals the Essential Role of Tafazzin in Cardiac Development and Function," Circulation Research, vol. 99, No. 2, pp. 201-208, (Jul. 21, 2006).

Houtkooper, et al., "The enigmatic role of tafazzin in cardiolipin metabolism," Biochimica Biophysica Acta, vol. 1788, No. 10, pp. 2003-2014, (2009).

Xu, et al., "Remodeling of Cardiolipin by Phospholipid Transacylation," The Journal of Biological Chemistry, vol. 278, No. 51, pp. 51380-51385, (Oct. 9, 2003).

Barth, et al., "X-Linked Cardioskeletal Myopathy and Neutropenia (Barth Syndrome): An Update," American Journal of Medical Genetics, vol. 126A, No. 4, pp. 349-354, (2004).

Neustein, et al., "An X-Linked Recessive Cardiomyopathy with Abnormal Mitochondria," Pediatrics, vol. 64, No. 1, pp. 24-29, (Jul. 1979).

Barth, et al., "X-linked cardioskeletal myopathy and neutropenia (Barth syndrome) (MIM 302060)," J Inherit Metab Dis, vol. 22, No. 4, pp. 555-567, (1999).

Kiebish, et al., "Dysfunctional cardiac mitochondrial bioenergetic, lipidomic, and signaling in a murine model of Barth syndrome," Journal of Lipid Research, vol. 54, No. 5, pp. 1312-1325, (Feb. 12, 2013).

Pfeiffer, et al., "Cardiolipin Stabilizes Respiratory Chain Supercomplexes," The Journal of Biological Chemistry, vol. 278, No. 52, pp. 52873-52880, (Oct. 15, 2003).

McKenzie, et al., "Mitochondrial Respiratory Chain Supercomplexes Are Destabilized in Barth Syndrome Patients," J Mol. Biol., vol. 361, No. 3, pp. 462-469, (2006).

Zhang, et al., "Gluing the Respiratory Chain Together: Cardiolipin Is Required for Supercomplex Formation in the Inner Mitochondrial Membrane," The Journal of Biological Chemistry, vol. 277, No. 46, pp. 43553-43556, (Oct. 2, 2002).

Zhang, et al., "Cardiolipin Is Essential for Organization of Complexes III and IV Into a Supercomplex in Intact Yeast Mitochondria," The Journal of Biological Chemistry, vol. 280, No. 33, pp. 29403-29408, (Aug. 19, 2005).

Baile, et al., "Unremodeled and Remodeled Cardiolipin Are Functionally Indistinguishable in Yeast," The Journal of Biological Chemistry, vol. 289, No. 3, pp. 1768-1778, (Nov. 27, 2013).

Sag, et al., "Redox regulation of cardiac hypertrophy," Journal of Molecular and Cell Cardiology, vol. 73, pp. 103-111, (2014).

(56) References Cited

OTHER PUBLICATIONS

Dai, et al., "Mitochondrial Oxidative Stress Mediates Angiotensin II-Induced Cardiac Hypertrophy and Gαq Overexpression-Induced Heart Failure," Circulation Research, vol. 108, No. 7, pp. 837-846, (2011).
Murphy, et al., "Unraveling the Biological Roles of Reactive Oxygen Species," Cell Metabolism, vol. 13, No. 4, pp. 361-366, (Apr. 6, 2011).
Acehan, et al., "Cardiac and Skeletal Muscle Defects in a Mouse Model of Human Barth Syndrome," The Journal of Biological Chemistry, vol. 286, No. 2, pp. 899-908, (Nov. 9, 2010).
Phoon, et al., "Tafazzin Knockdown in Mice Leads to a Developmental Cardiomyopathy With Early Diastolic Dysfunction Preceding Myocardial Noncompaction," Journal of American Heart Association, vol. 1, No. 2, pp. 1-13, (Apr. 13, 2012).
Soustek, et al., "Characterization of a Transgenic Short Hairpin RNA-Induced Murine Model of Tafazzin Deficiency," Human Gene Therapy, vol. 22, No. 7, pp. 865-871, (Jul. 2011).
Pisani, et al., "Enzyme replacement therapy in patients with Fabry disease: State of the art and review of the literature," Molecular Genetics and Metabolism, vol. 107, No. 3, pp. 267-275, (2012).
Liu, et al., "Transcription factor CHF1/Hey2 regulates EC coupling and heart failure in mice through regulation of FKBP12.6," American Journal of Physiology Heart and Circulatory Physiology, vol. 302, No. 9, pp. H1860-H1870, (Mar. 9, 2012).
Rapoport, et al., "TAT-mediated Delivery of LAD Restores Pyruvate Dehydrogenase Complex Activity in the Mitochondria of Patients With LAD Deficiency," Molecular Therapy: The Journal of the American Society of Gene Therapy, vol. 16, No. 4, pp. 691-697, (Apr. 2008).
Schwarze, et al., "Protein transduction: unrestricted delivery into all cells?" Trends in Cell Biology, vol. 10, No. 7, pp. 290-295, (Jul. 2000).
Zhou, et al., "Generation of Induced Pluripotent Stern Cells Using Recombinant Proteins," Cell Stem Cell, vol. 4, No. 5, pp. 381-384, (May 8, 2009).
Zahid, et al., "Identification of a Cardiac Specific Protein Transduction Domain by In Vivo Biopanning Using a M13 Phage Peptide Display Library in Mice," PLoS One, vol. 5, No. 8, e12252, pp. 1-11, (Aug. 2010).
N'Guessan, et al., "Evaluation of quantitative and qualitative aspects of mitochondrial function in human skeletal and cardiac muscles," Molecular and Cellular Biochemistry, vol. 256/257, No. 1/2, pp. 267-280, (2004).
Xiang, et al., "Transcription factor CHF1/Hey2 suppresses cardiac hypertrophy through an inhibitory interaction with GATA4," Am J Physiol Heart Circ Physiol., vol. 290, No. 5, pp. H1997-H2006, (2006).
Springhorn, et al., "Preproenkephalin mRNA expression in developing rat heart and in cultured ventricular cardiac muscle cells," Biochem J., vol. 258, No. 1, pp. 73-78, (1989).
Liu, et al., "The bHLH transcription factor CHF1/HEY2 regulates susceptibility to apoptosis and heart failure after pressure overload," Am J Physiol Heart Circ Physiol., vol. 298, No. 6, pp. H2082-H2092, (2010).
Yu, et al., "CHF1/Hey2 Promotes Physiological Hypertrophy in Response to Pressure Overload through Selective Repression and Activation of Specific Transcriptional Pathways," OMICS A Journal of Integrative Biology, vol. 13, No. 6, pp. 501-511, (Nov. 6, 2009).
Vermes, et al., "A novel assay for apoptosis Flow cytometric detection of phosphatidylserine expression on early apoptotic cells using fluorescein labelled Annexin V," Journal of Immunological Methods, vol. 184, No. 1, pp. 39-51, (1995).
Schutte, et al., "Annexin V binding assay as a tool to measure apoptosis in differentiated neuronal cells," Journal of Neuroscience Methods, vol. 86, No. 1, pp. 63-69, (1998).
Liao, et al., "Cardiac-Specific Overexpression of GLUT1 Prevents the Development of Heart Failure Attributable to Pressure Overload in Mice," Circulation, vol. 106, No. 16, pp. 2125-2131, (2002).
International Search Report and Written Opinion received Apr. 1, 2016 in International Patent Application No. PCT/US2015/065235.

* cited by examiner

FIG. 9

MODIFIED TAFAZZIN PROTEINS AND METHODS OF MAKING AND USING THE SAME

CROSS-REFERENCE TO RELATED APPLICATIONS

This application claims the benefit of U.S. Provisional Application No. 61/930,264, filed Jan. 22, 2014, which is hereby incorporated by reference in its entirety.

TECHNICAL FIELD

The present disclosure relates generally to fusion proteins comprising a tafazzin peptide and a cellular permeability peptide and methods of making and using the same. In particular, the present disclosure relates to fusion proteins comprising a tafazzin peptide coupled to a permeability peptide through a polypeptide linker. More particularly, the present disclosure relates to methods of using the fusion proteins to treat a patient having a disorder associated with a tafazzin deficiency or a remodeled cardiolipin deficiency (e.g., Barth syndrome). Even more particularly, the present disclosure relates to use of the fusion proteins in prophylaxis against developing a disorder associated with a tafazzin deficiency or a remodeled cardiolipin deficiency in a patient at risk of developing such a disorder.

BACKGROUND

Tafazzin (TAZ) is a mitochondrial transacylase that can catalyze the transfer of acyl chains from phosphatidyl choline to cardiolipin (CL), remodeling monolysocardiolipin (MLCL) to tetralinoleoyl cardiolipin (L4CL) (see Houtkooper R H, et al. (2009) Biochim. Biophys. Acta 1788, 2003-2014 and Xu Y, et al. (2003) J. Biol. Chem. 278, 51380-51385). Mutations in TAZ can result in impairment of lipid metabolism (see Aprikyan A A and Khuchua Z. (2013) Brit. J. Haematol. 161, 330-338) leading to mitochondrial dysfunction, which can be manifested clinically, for example, in highly energetic tissues such as the heart and skeletal muscle (see id. and Khuchua Z, et al. (2006) Circ. Res. 99, 201-208).

Studies have shown that CL, a structurally unique phospholipid component of the inner mitochondrial membrane, can provide functional support for electron transport chain complexes (see Kiebish M A, et al. (2013) J. Lipid Res. 54, 1312-1325 and Pfeiffer K, et al. (2003) J. Biol. Chem. 278, 52873-52880). In the absence of CL, respiratory supercomplex formation can be hindered (see McKenzie M, et al. (2006) J. Mol. Biol. 361, 462-469 and Zhang M, Mileykovskaya E, Dowhan W (2002) J. Biol. Chem. 277, 43553-43556) and individual complex activity can be decreased (see Zhang M, Mileykovskaya E, Dowhan W. (2005) J. Biol. Chem. 280, 29403-29408). Additionally, disturbances in the acyl chain composition of CL have been linked to impaired mitochondrial respiratory function (see Xu Y, et al. (2003) J. Biol. Chem. 278, 51380-51385), possibly through alteration in membrane dynamics (see Baile M G, et al. (2014) J. Biol. Chem. 289, 1768-1778).

It has been reported that cardiomyocytes (CMs) derived from induced pluripotent stem cells (iPS cells) containing targeted TAZ mutations demonstrate substantially normal ATP stores but increased reactive oxygen species (ROS) (Wang G, et al. (2014) Nat. Med. 20, 616-623). ROS have been implicated in the pathogenesis of cardiac hypertrophy and regulation of excitation-contraction coupling through effects on specific signaling pathways such as ERK, AKT, and PKA (see Sag C M, Santos C X, Shah A M (2014) J. Mol. Cell Cardiol. 73C, 103-111). Mitochondrial ROS, in particular, have been associated with angiotensin H-induced hypertrophy and heart failure associated with Gαq signaling (see Dai D F, et al. (2011) Circ. Res. 108, 837-846). Excessive ROS have also been linked to apoptosis (see Murphy M P, et al. (2011) Cell Metab. 13, 361-366).

Tafazzin orthologs are present in a wide variety of model organisms, indicating tafazzin's importance in mitochondrial biology, and providing the opportunity for the study of tafazzin function in organisms as diverse as, but not limited to, yeast, drosophila, and mice. In humans, the tafazzin gene is expressed via multiple splice variants, at least two of which have enzymatic activity. In experimental models of heart failure, such as the spontaneously hypertensive rat model, and in tissue samples collected from patients with heart failure, tafazzin expression and remodeled cardiolipin levels are reduced, suggesting that TAZ may play a common role in multiple forms of heart failure (see Sparagna G C, et al. (2007) J. Lipid Res. 48, 1559-1570). Since striated muscle cells generally require ATP for contraction, defects in mitochondrial function may lead to diminished ATP stores and consequent contractile dysfunction, as suggested previously (see He Q (2010) Am. J. Physiol.-Heart C. 299, H210-H216).

Barth syndrome (BTHS) is an X-linked disorder that is often characterized by mitochondrial functional impairment resulting in cardiac and skeletal myopathies, cyclic neutropenia, hypotonia, and 3-methylglutaconic aciduria (see Barth P G, et al. (2004) Am. J. Med. Genet. Part A 126A, 349-354). BTHS mitochondria can also appear morphologically abnormal and mitochondrial respiration can be impaired. TAZ has been linked with BTHS (see Xu Y, et al. (2006) J. Biol. Chem. 281, 39217-39224). Clinically, the cardiomyopathy observed in BTHS patients is primarily dilated cardiomyopathy and usually presents in the first year of life, although noncompaction cardiomyopathy has also been observed both clinically (see Bleyl S B, et al. (1997) Am. J. Med. Genet. 72, 257-265) and experimentally (see Phoon C K L, et al. (2012) J Am. Heart Assoc. 1, jah3-e000455-jah000453-e000455). Skeletal muscle weakness is also present early in life in BTHS patients, and neutropenia can vary, ranging from mild depression to complete absence, often in the same patient and often triggered by infection. Mortality was reportedly highest in infancy and childhood in early studies, but more recently, better diagnosis and treatment has improved survival, although few BTHS patients survive beyond middle age. At present, no specific therapy is available for BTHS patients.

The role of TAZ mutations in the pathogenesis of cardiomyopathy in BTHS has traditionally been ascribed to ATP deficiency due to the inefficient mitochondrial respiration observed in TAZ-deficient cells; however, it has been suggested that excessive production of reactive oxygen species (ROS) may be a more likely cause (see Wang G, et al. (2014) Nat. Med. 20, 616-623). Reduced levels of TAZ have also been observed in other forms of experimental heart failure and in clinical samples from patients with heart failure, raising the possibility that abnormalities in TAZ-dependent mitochondrial function may serve as a final common pathway for heart failure (see Sparagna G C, et al. (2007) 48, 1559-1570).

At the cellular level, hearts from BTHS patients can demonstrate morphologically abnormal mitochondria (see Neustein H B, et al. (1979) Pediatrics 64, 24-29) while fibroblasts can demonstrate impaired mitochondrial respiration due to deficiency of Complex III and IV activity (see Barth P G, et al. (1996) J. Inherit. Metab. Dis. 19, 157-160). Cultured fibroblasts can also demonstrate severe depletion of tetralinoleoyl cardiolipin (see Valianpour F, et al. (2003) J. Lipid Res, 44, 560-566 and Valianpour F, et al. (2002) J. Pediatr. 141, 729-733) that could be rescued by linoleic acid supplementation. Similarly, heart tissue can also demonstrate deficiency of tetralinoleoyl cardiolipin in the absence of functional tafazzin (see Schlame M, et al. (2002) Ann. Neurol. 51, 634-637).

A mouse model of inducible tafazzin deficiency has been developed, which can recapitulate many of the clinical manifestations of BTHS (see Acehan D, et al. (2011) J. Biol. Chem. 286, 899-908; Phoon C K L, et al. (2012) J Am. Heart Assoc. 1, jah3-e000455-jah000453-e000455; and Soustek M S, et al. (2011) Hum. Gene Ther. 22, 865-871). Characterization of this mouse model has revealed defects in cardiolipin modification, mitochondrial morphology, and both cardiac and skeletal muscle function. At baseline, however, these mice do not generally demonstrate any appreciable, or substantially appreciable, cardiac dysfunction until the age of 8 months, suggesting that additional stress may be required to trigger the onset of heart failure.

Nutritional supplementations with carnitine and linoleic acid have been promoted as potential treatments for BTHS, but results have been disappointing. Skeletal myopathy is generally difficult to treat. Heart failure in BTHS patients can be treated supportively, with diuretics, afterload reduction, beta blockade, and mechanical support as a bridge to transplant in severe cases, which are standard treatments for most cases of systolic heart failure. Infections resulting from neutropenia are treated with antibiotics. Although these interventions can alleviate symptoms and possibly improve outcome in BTHS patients, they do not treat the underlying metabolic disorder.

BRIEF DESCRIPTION OF THE DRAWINGS

The embodiments disclosed herein will become more fully apparent from the following description and appended claims, taken in conjunction with the accompanying drawings.

FIG. 9 are micrographs depicting that recombinant tafazzin tagged with CTP localizes to mitochondria. H9c2 myoblasts were treated with untagged TAZ (top panel) or TAZ-CTP (bottom panel). Protein uptake was detected by immunofluorescence and mitochondrial colocalization was detected by overlap with mitotracker dye.

DETAILED DESCRIPTION

Figure 1A:
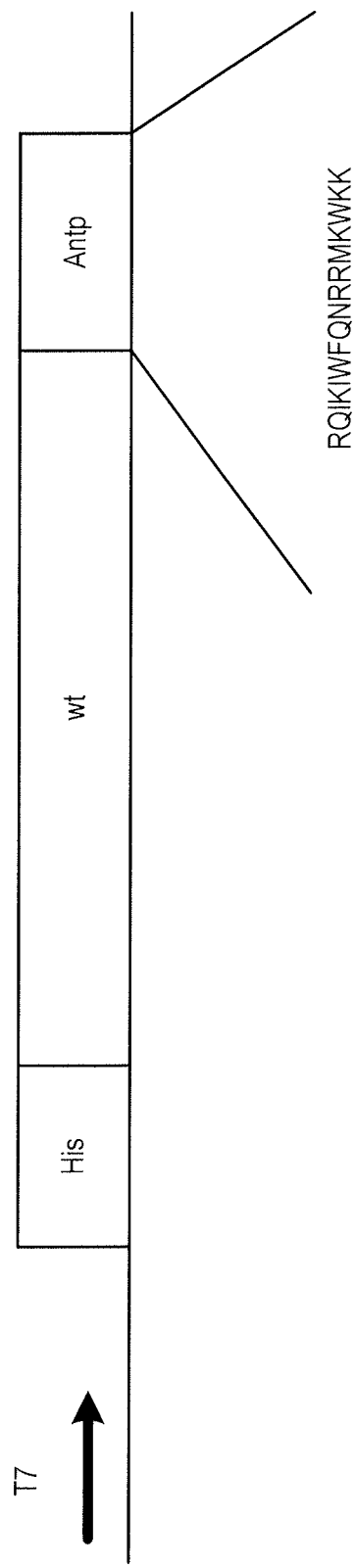
FIG. 1A is a tafazzin recombinant protein construct comprising a His tag in the N-terminus and an antennapedia (Antp) tag in the C-terminus.

The present disclosure relates generally to fusion proteins comprising a tafazzin peptide and a cellular permeability peptide and methods of making and using the same. The present disclosure also relates to fusion proteins comprising a tafazzin peptide coupled to a permeability peptide through a polypeptide linker. Further, the present disclosure relates to methods of using the fusion proteins to treat patients having one or more disorders associated with a tafazzin deficiency or a remodeled cardiolipin deficiency (e.g., Barth syndrome). The present disclosure also relates to prophylaxis against developing a disorder associated with a tafazzin deficiency or a remodeled cardiolipin deficiency in patients at risk of developing a disorder associated with a tafazzin deficiency or a remodeled cardiolipin deficiency.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, "Barth syndrome" refers to an X-linked disorder characterized by mutations in the TAZ gene that can result in mitochondrial functional impairment resulting in cardiac and skeletal myopathies, cyclic neutropenia, and 3-methylglutaconic aciduria.

As used herein, "tafazzin" refers to a phospholipid-lysophospholipid transacylase that can be responsible for modification of cardiolipin (a membrane phospholipid) to its tetralinoleoyl form. In some embodiments, tafazzin can refer to full-length human tafazzin or human tafazzin lacking exon 5, both of which can exhibit transacylase activity. In certain embodiments, tafazzin can refer to full-length mouse tafazzin, which is homologous to the human tafazzin lacking exon 5.

As used herein, "peptide" and "polypeptide" may be used in their broadest senses to refer to a sequence of subunit amino acids. The peptides or polypeptides of the disclosure may comprise L-amino acids, D-amino acids (which can be resistant to L-amino acid-specific proteases in vivo), or a combination of D- and L-amino acids. The terms peptide and polypeptide can be used interchangeably. The peptides and polypeptides described herein may be chemically synthesized or recombinantly expressed. The peptides and polypeptides may be linked to any other moiety as deemed useful for a given purpose. Such linkage can comprise covalent linkages or non-covalent linkages as is understood by those of skill in the art.

As used herein, "fusion proteins" and "chimeric proteins" refer to proteins created through the joining of two or more genes (e.g., a fusion gene), each of which originally coded for separate proteins. Translation of a fusion gene may result in one or more polypeptides comprising functional properties derived from each of the two or more genes.

As used herein, a "cellular permeability peptide" refers to a peptide that facilitates cellular uptake of the peptide itself and other peptides that are linked to the cellular permeability peptide. In certain embodiments these peptides can comprise portions of *Drosophila* antennapedia, HIV Tat, cardiac targeting, and Kaposi FGF4 peptides, which may facilitate cellular uptake. As used herein, such peptide fragments may be referred to as antennapedia permeability peptides, HIV Tat permeability peptides, cardiac targeting permeability peptides, and Kaposi FGF4-permeability peptides.

Amino acid residues as disclosed herein can be modified by conservative substitutions to maintain, or substantially maintain, overall polypeptide structure and/or function. As used herein, "conservative amino acid substitution" indicates that: hydrophobic amino acids (i.e., Ala, Cys, Gly, Pro, Met, Sce, Sme, Val, Ile, and Leu) can be substituted with other hydrophobic amino acids; hydrophobic amino acids with bulky side chains (i.e., Phe, Tyr, and Trp) can be substituted with other hydrophobic amino acids with bulky side chains; amino acids with positively charged side chains (i.e., Arg, His, and Lys) can be substituted with other amino acids with positively charged side chains; amino acids with negatively charged side chains (i.e., Asp and Glu) can be substituted with other amino acids with negatively charged side chains; and amino acids with polar uncharged side chains (i.e., Ser, Thr, Asn, and Gln) can be substituted with other amino acids with polar uncharged side chains.

Treating a subject can comprise delivering an effective amount or delivering a prophylactic treatment and/or a therapeutic treatment to a subject (e.g., a patient). An "effective amount" is an amount of a compound that can result in a desired physiological change in a subject. Effective amounts may also be administered for research purposes.

A "prophylactic treatment" comprises a treatment administered to a subject who does not display signs or symptoms of a disease or condition, or a subject who displays only early signs or symptoms of a disease or condition, such that treatment is administered for the purpose of diminishing, preventing, and/or decreasing the risk of further developing the disease or condition or of diminishing, preventing, and/or decreasing the risk of developing the disease or condition. Thus, a prophylactic treatment may function as a preventative treatment against a disease or condition.

A "therapeutic treatment" comprises a treatment administered to a subject who displays symptoms or signs of a disease or a condition and the therapeutic treatment is administered to the subject for the purpose of diminishing or eliminating the symptoms or the signs of the disease or the condition.

"Therapeutically effective amounts" comprise amounts that provide prophylactic treatment and/or therapeutic treatment. Therapeutically effective amounts need not fully prevent or cure the disease or the condition but can also provide a partial benefit, such as a delay of onset or an alleviation or an improvement of at least one symptom of the disease or the condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the $IC_{50}$ as determined in cell culture. Such information can be used to more accurately determine useful doses in subjects of interest.

The actual dose amount administered to a particular subject can be determined by a physician, a veterinarian, or a researcher, taking into account parameters such as, but not limited to, physical and physiological factors including body weight, severity of condition, type of disease, previous or concurrent therapeutic interventions, idiopathy of the subject, and/or route of administration.

Doses can range from 0.1 mg/kg/day to 5 mg/kg/day or from 0.5 mg/kg/day to 1 mg/kg/day or from 0.1 mg/kg/day to 5 μg/kg/day or from 0.5 mg/kg/day to 1 μg/kg/day. In other non-limiting examples, a dose can comprise 1 μg/kg/day, 5 μg/kg/day, 10 μg/kg/day, 50 μg/kg/day, 100 μg/kg/day, 200 μg/kg/day, 350 μg/kg/day, 500 μg/kg/day, mg/kg/day, 5 mg/kg/day, 10 mg/kg/day, 50 mg/kg/day, 100 mg/kg/day, 200 mg/kg/day, 350 mg/kg/day, 500 mg/kg/day, or 1000 mg/kg/day. Therapeutically effective amounts can be achieved by administering single or multiple doses during the course of a treatment regimen (i.e., days, weeks, months, etc.).

In some embodiments, at least one compound is provided as part of a pharmaceutical composition. The pharmaceutical composition can comprise, for example, at least 0.1% w/v of a compound. In some other embodiments, the pharmaceutical composition can comprise between 2% to 75% of compound per weight of the pharmaceutical composition, or between 25% to 60% of compound per weight of the pharmaceutical composition.

Pharmaceutically acceptable salts, tautomers, and isomers of the compounds disclosed herein can also be used. Exemplary salts can include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The formulations described herein can be administered by, without limitation, injection, inhalation, infusion, perfusion, lavage, and/or ingestion. Routes of administration can include, but are not limited to, intravenous, intradermal, intraarterial, intraperitoneal, intralesional, intracranial, intraarticular, intraprostatic, intrapleural, intratracheal, intranasal, intravitreal, intravaginal, intrarectal, topically, intratumoral, intramuscular, intravesicular, intrapericardial, intraumbilical, intraocularal, mucosal, oral, subcutaneous, and/or subconjunctival.

In some embodiments, for injection, formulations can be made as aqueous solutions, such as in buffers including, but not limited to, Hanks' solution, Ringer's solution, and/or physiological saline. The solutions can contain formulatory agents such as suspending, stabilizing, and/or dispersing agents. Alternatively, the formulation can be in lyophilized and/or powder form for constitution with a suitable vehicle control (e.g., sterile pyrogen-free water) before use.

Any formulation disclosed herein can advantageously comprise any other pharmaceutically acceptable carrier or carriers which comprise those that do not produce significantly adverse, allergic, or other untoward reactions that may outweigh the benefit of administration, whether for research, prophylactic, and/or therapeutic treatments. Exemplary pharmaceutically acceptable carriers and formulations are disclosed in Remington's Pharmaceutical Sciences, 18th Ed., Mack Printing Company, 1990, which is incorporated by reference herein for its teachings regarding the same. Moreover, formulations can be prepared to meet sterility, pyrogenicity, general safety, and purity standards as required by the United States FDA's Division of Biological Standards and Quality Control and/or other relevant U.S. and foreign regulatory agencies.

Exemplary, generally used pharmaceutically acceptable carriers may comprise, but are not limited to, bulking agents or fillers, solvents or co-solvents, dispersion media, coatings, surfactants, antioxidants (e.g., ascorbic acid, methionine, and vitamin E), preservatives, isotonic agents, absorption delaying agents, salts, stabilizers, buffering agents, chelating agents (e.g., EDTA), gels, binders, disintegration agents, and/or lubricants.

Exemplary buffering agents may comprise, but are not limited to, citrate buffers, succinate buffers, tartrate buffers, fumarate buffers, gluconate buffers, oxalate buffers, lactate buffers, acetate buffers, phosphate buffers, histidine buffers, and/or trimethylamine salts.

Exemplary preservatives may comprise, but are not limited to, phenol, benzyl alcohol, meta-cresol, methylparaben, propyl paraben, octadecyldimethylbenzyl ammonium chloride, benzalkonium halides, hexamethonium chloride, alkyl parabens (such as methyl or propyl paraben), catechol, resorcinol, cyclohexanol, and/or 3-pentanol.

Exemplary isotonic agents may comprise polyhydric sugar alcohols comprising, but not limited to, trihydric or higher sugar alcohols, (e.g., glycerin, erythritol, arabitol, xylitol, sorbitol, and/or mannitol).

Exemplary stabilizers may comprise, but are not limited to, organic sugars, polyhydric sugar alcohols, polyethylene glycol, sulfur-containing reducing agents, amino acids, low molecular weight polypeptides, proteins, immunoglobulins, hydrophilic polymers, and/or polysaccharides.

Formulations can also be depot preparations. In some embodiments, such long-acting formulations may be administered by, without limitation, implantation (e.g., subcutaneously or intramuscularly) or by intramuscular injection. Thus, for example, compounds can be formulated with suitable polymeric and/or hydrophobic materials (e.g., as an emulsion in an acceptable oil) or ion exchange resins, or as sparingly soluble derivatives (e.g., as a sparingly soluble salt).

Additionally, in various embodiments, compounds can be delivered using sustained-release systems, such as semipermeable matrices of solid polymers comprising at least one compound. Various sustained-release materials have been established and are well known by those of ordinary skill in the art. Sustained-release capsules may, depending on their chemical nature, release the compound following administration for a few weeks up to over 100 days.

A first aspect of the disclosure relates to a fusion protein comprising a tafazzin peptide and a cellular permeability peptide. In some embodiments, the fusion protein may be isolated and/or purified. Additionally, the fusion protein comprising the tafazzin peptide and the cellular permeability peptide may comprise a peptide selected from the group consisting of SEQ ID NO: 1 (human TAZ wild type full length [NCBI RefSeq no. NP_000107.1]), SEQ ID NO: 2 (human TAZ wild type lacking exon 5 [NCBI RefSeq no. NP_851828.1]), SEQ ID NO: 3 (mouse TAZ wild type [NCBI RefSeq no. NP_852657.1]), SEQ ID NO: 4 (human-mouse chimeric protein), and SEQ ID NO: 5 (mouse-human chimeric protein).

In some embodiments, the fusion protein comprising the tafazzin peptide and the cellular permeability peptide may comprise a peptide that is at least eighty percent identical to at least one of SEQ ID NO: 1, SEQ ID NO: 2, SEQ ID NO: 3, SEQ ID NO: 4, and SEQ ID NO: 5. In other embodiments, the fusion protein comprising the tafazzin peptide and the cellular permeability peptide may comprise a peptide that is at least sixty percent identical to at least one of SEQ ID NO: 1, SEQ ID NO: 2, SEQ ID NO: 3, SEQ ID NO: 4, and SEQ ID NO: 5. In yet other embodiments, the fusion protein comprising the tafazzin peptide and the cellular permeability peptide may comprise a peptide that is at least forty percent identical to at least one of SEQ ID NO: 1, SEQ ID NO: 2, SEQ ID NO: 3, SEQ ID NO: 4, and SEQ ID NO: 5. In still other embodiments, the fusion protein comprising the tafazzin peptide and the cellular permeability peptide may comprise a peptide that is at least twenty percent identical to at least one of SEQ ID NO: 1, SEQ ID NO: 2, SEQ ID NO: 3, SEQ ID NO: 4, and SEQ ID NO: 5.

In certain embodiments, the cellular permeability peptide may comprise an antennapedia permeability peptide. For example, the fusion protein may comprise a tafazzin peptide and an antennapedia permeability peptide. The fusion protein may also comprise a tafazzin peptide coupled to an antennapedia permeability peptide. In some embodiments, the antennapedia permeability peptide may comprise SEQ ID NO: 6 (Antennapedia permeability peptide).

In various embodiments, the antennapedia permeability peptide may comprise a peptide that is at least eighty percent identical to SEQ ID NO: 6. In other embodiments, the antennapedia permeability peptide may comprise a peptide that is at least sixty percent identical to SEQ ID NO: 6. In yet other embodiments, the antennapedia permeability peptide may comprise a peptide that is at least forty percent identical to SEQ ID NO: 6. In still other embodiments, the antennapedia permeability peptide may comprise a peptide that is at least twenty percent identical to SEQ ID NO: 6.

In some other embodiments, the cellular permeability peptide may comprise an HIV Tat permeability peptide. For example, the fusion protein may comprise a tafazzin peptide and an HIV Tat permeability peptide. The fusion protein may also comprise a tafazzin peptide coupled to an HIV Tat permeability peptide. In some embodiments, the HIV Tat permeability peptide may comprise SEQ ID NO: 7 (HIV Tat permeability peptide).

In certain embodiments, the HIV Tat permeability peptide may comprise a peptide that is at least eighty percent identical to SEQ ID NO: 7. In other embodiments, the HIV Tat permeability peptide may comprise a peptide that is at least sixty percent identical to SEQ ID NO: 7. In yet other embodiments, the HIV Tat permeability peptide may comprise a peptide that is at least forty percent identical to SEQ ID NO: 7. In still other embodiments, the HIV Tat permeability peptide may comprise a peptide that is at least twenty percent identical to SEQ ID NO: 7.

In some other embodiments, the cellular permeability peptide may comprise a cardiac targeting peptide (CTP). For example, the fusion protein may comprise a tafazzin peptide and a CTP. The fusion protein may also comprise a tafazzin peptide coupled to a CTP. In some embodiments, the CTP may comprise SEQ ID NO: 8 (Cardiac Targeting Peptide [CTP]).

In certain embodiments, the CTP may comprise a peptide that is at least eighty percent identical to SEQ ID NO: 8. In other embodiments, the CTP may comprise a peptide that is at least sixty percent identical to SEQ ID NO: 8. In yet other embodiments, the CTP may comprise a peptide that is at least forty percent identical to SEQ ID NO: 8. In still other embodiments, the CTP may comprise a peptide that is at least twenty percent identical to SEQ ID NO: 8.

In some other embodiments, the cellular permeability peptide may comprise a Kaposi FGF4-permeability peptide. For example, the fusion protein may comprise a tafazzin peptide and a Kaposi FGF4-permeability peptide. The fusion protein may also comprise a tafazzin peptide coupled to a Kaposi FGF4-permeability peptide. In some embodiments, the Kaposi FGF4-permeability peptide may comprise SEQ ID NO: 9 (Kaposi FGF4-derived peptide).

In various embodiments, the Kaposi FGF4-permeability peptide may comprise a peptide that is at least eighty percent identical to SEQ ID NO: 9. In other embodiments, the Kaposi FGF4-permeability peptide may comprise a peptide that is at least sixty percent identical to SEQ ID NO: 9. In yet other embodiments, the Kaposi FGF4-permeability peptide may comprise a peptide that is at least forty percent identical to SEQ ID NO: 9. In still other embodiments, the Kaposi FGF4-permeability peptide may comprise a peptide that is at least twenty percent identical to SEQ ID NO: 9.

In some embodiments, the tafazzin peptide may be coupled to the cellular permeability peptide (e.g., an antennapedia permeability peptide, an HIV Tat permeability peptide, a CTP, or a Kaposi FGF4-permeability peptide) through or via a polypeptide linker. In certain embodiments, the tafazzin peptide coupled to the cellular permeability peptide through or via the polypeptide linker may comprise a peptide selected from the group consisting of SEQ ID NO: 10 (mouse TAZ-Antp), SEQ ID NO: 11 (human TAZ-Antp), SEQ ID NO: 12 (mouse TAZ-CTP), and SEQ ID NO: 13 (human TAZ-CTP). In various embodiments the polypeptide linker may comprise a peptide selected from the group consisting of SEQ ID NO: 14, SEQ ID NO: 15, SEQ ID NO: 16, and SEQ ID NO: 17.

In certain embodiments, the tafazzin peptide coupled to the cellular permeability peptide through a polypeptide linker may comprise a peptide that is at least eighty percent identical to at least one of SEQ ID NO: 10, SEQ ID NO: 11, SEQ ID NO: 12, and SEQ ID NO: 13. In other embodiments, the tafazzin peptide coupled to the cellular permeability peptide through a polypeptide linker may comprise a peptide that is at least sixty percent identical to at least one of SEQ ID NO: 10, SEQ ID NO: 11, SEQ ID NO: 12, and SEQ ID NO: 13. In yet other embodiments, the tafazzin peptide coupled to the cellular permeability peptide through a polypeptide linker may comprise a peptide that is at least forty percent identical to at least one of SEQ ID NO: 10, SEQ ID NO: 11, SEQ ID NO: 12, and SEQ ID NO: 13. In still other embodiments, the tafazzin peptide coupled to the cellular permeability peptide through a polypeptide linker may comprise a peptide that is at least twenty percent identical to at least one of SEQ ID NO: 10, SEQ ID NO: 11, SEQ ID NO: 12 and SEQ ID NO: 13.

Another aspect of the disclosure relates to methods of treating a patient having a disorder associated with a tafazzin deficiency.

In some embodiments, this disclosure provides methods of treating a patient having a disorder associated with a tafazzin deficiency comprising administering to the patient an effective amount of a pharmaceutical composition comprising a fusion protein comprising a tafazzin peptide and a cellular permeability peptide. The effective amount of the pharmaceutical composition comprising the tafazzin peptide and the cellular permeability peptide may also comprise a pharmaceutically acceptable carrier.

In certain embodiments, the methods of treating a patient having a disorder associated with a tafazzin deficiency may comprise administering to the patient an effective amount of a pharmaceutical composition comprising a fusion protein comprising a tafazzin peptide and a cellular permeability peptide to reduce a pathological effect or symptom of the disorder associated with the tafazzin deficiency. As discussed above, the effective amount of the pharmaceutical composition comprising the tafazzin peptide and the cellular permeability peptide may also comprise a pharmaceutically acceptable carrier.

In various embodiments, the pathological effect or symptom of the disorder associated with the tafazzin deficiency may comprise at least one of skeletal myopathy, neutropenia, hypotonia, 3-methylglutaconic aciduria, morphologically abnormal mitochondria, and/or impaired mitochondrial respiration.

In some embodiments, the tafazzin deficiency may be associated with a tafazzin gene (TAZ) mutation. In certain embodiments, the disorder associated with the tafazzin deficiency may be Barth syndrome.

Another aspect of the disclosure relates to methods of treating a patient having a disorder associated with a remodeled cardiolipin deficiency.

In some embodiments, this disclosure provides methods of treating a patient having a disorder associated with a remodeled cardiolipin deficiency comprising administering to the patient an effective amount of a pharmaceutical composition comprising a fusion protein comprising a tafazzin peptide and a cellular permeability peptide. The effective amount of the pharmaceutical composition comprising the tafazzin peptide and the cellular permeability peptide may also comprise a pharmaceutically acceptable carrier.

In certain embodiments, the methods of treating a patient having a disorder associated with a remodeled cardiolipin deficiency may comprise administering to the patient an effective amount of a pharmaceutical composition comprising a fusion protein comprising a tafazzin peptide and a cellular permeability peptide to reduce a pathological effect or symptom of the disorder associated with the remodeled cardiolipin deficiency. As discussed above, the effective amount of the pharmaceutical composition comprising the tafazzin peptide and the cellular permeability peptide may also comprise a pharmaceutically acceptable carrier.

In various embodiments, the pathological effect or symptom of the disorder associated with the a remodeled cardiolipin deficiency may comprise at least one of skeletal myopathy, neutropenia, hypotonia, 3-methylglutaconic aciduria, morphologically abnormal mitochondria, and/or impaired mitochondrial respiration.

In some embodiments, the remodeled cardiolipin deficiency may be associated with a tafazzin gene (TAZ) mutation. In certain embodiments, the disorder associated with the remodeled cardiolipin deficiency may be Barth syndrome.

Another aspect of the disclosure relates to methods of prophylaxis against a risk of developing a disorder associated with a tafazzin deficiency or a remodeled cardiolipin deficiency in a patient.

In some embodiments, this disclosure provides methods of prophylaxis against a risk of developing a disorder associated with a tafazzin deficiency or a remodeled cardiolipin deficiency in a patient, comprising administering to the patient an effective amount of a pharmaceutical composition comprising a fusion protein comprising a tafazzin peptide and a cellular permeability peptide. The effective amount of the pharmaceutical composition comprising the tafazzin peptide and the cellular permeability peptide may also comprise a pharmaceutically acceptable carrier.

In certain embodiments, the methods of prophylaxis against a risk of developing a disorder associated with a tafazzin deficiency or a remodeled cardiolipin deficiency in a patient may comprise administering to the patient an effective amount of a pharmaceutical composition comprising a fusion protein comprising a tafazzin peptide and a cellular permeability peptide to reduce the risk of developing a disorder associated with the tafazzin deficiency or the remodeled cardiolipin deficiency. As discussed above, the effective amount of the pharmaceutical composition comprising the tafazzin peptide and the cellular permeability peptide may also comprise a pharmaceutically acceptable carrier.

Another aspect of the disclosure relates to methods of treating a patient having Barth syndrome.

In some embodiments, this disclosure provides methods of treating a patient having Barth syndrome comprising administering to the patient an effective amount of a pharmaceutical composition comprising a fusion protein comprising a tafazzin peptide and a cellular permeability peptide. The effective amount of the pharmaceutical composition comprising the tafazzin peptide and the cellular permeability peptide may also comprise a pharmaceutically acceptable carrier.

In certain embodiments, the methods of treating a patient having Barth syndrome may comprise administering to the patient an effective amount of a pharmaceutical composition comprising a fusion protein comprising a tafazzin peptide and a cellular permeability peptide to reduce a pathological effect or symptom of Barth syndrome. As discussed above, the effective amount of the pharmaceutical composition comprising the tafazzin peptide and the cellular permeability peptide may also comprise a pharmaceutically acceptable carrier.

In various embodiments, the pathological effect or symptom of Barth syndrome may comprise at least one of skeletal myopathy, neutropenia, hypotonia, 3-methylglutaconic aciduria, morphologically abnormal mitochondria, and/or impaired mitochondrial respiration.

Another aspect of the disclosure relates to methods of prophylaxis against a risk of developing Barth syndrome.

In some embodiments, this disclosure provides methods of prophylaxis against a risk of developing Barth syndrome in a patient comprising administering to the patient an effective amount of a pharmaceutical composition comprising a fusion protein comprising a tafazzin peptide and a cellular permeability peptide. The effective amount of the pharmaceutical composition comprising the tafazzin peptide and the cellular permeability peptide may also comprise a pharmaceutically acceptable carrier.

In certain embodiments, the methods of prophylaxis against a risk of developing Barth syndrome in a patient may comprise administering to the patient an effective amount of a pharmaceutical composition comprising a fusion protein comprising a tafazzin peptide and a cellular permeability peptide to reduce the risk of developing Barth syndrome. As discussed above, the effective amount of the pharmaceutical composition comprising the tafazzin peptide and the cellular permeability peptide may also comprise a pharmaceutically acceptable carrier.

In some embodiments, enzyme replacement therapy can comprise the replacement enzyme reaching one or more target locations of the replacement enzyme within a cell. Tafazzin protein is generally localized to the mitochondria. In some embodiments, exogenous tafazzin protein can first enter the cell and then localize to the mitochondria. It has been demonstrated that certain peptide sequences (e.g., cellular permeability peptides (CPPs)) can promote the uptake of proteins coupled to or comprising CPPs into cells (see Frankel, A. D., and Pabo, C. O. (1988) Cell 55, 1189-1193; and Min, S. H., et al. (2010) Biomaterials 31, 1858-1864). In some embodiments, as discussed above, the CPP may be derived from an HIV Tat protein, *Drosophila* antennapedia protein, etc. (id.). A peptide that reportedly targets the heart (see Zahid, M., et al. (2010) PLoS One 5, e12252) has also been tested. In certain embodiments, a recombinant tafazzin protein incorporating a CPP may enter tafazzin deficient cells, localize to the mitochondria, and/or catalyze the modification of cardiolipin.

In various embodiments, restoration of cardiolipin modification may restore mitochondrial function. For example, restoration of mitochondrial function may ameliorate myocyte dysfunction. Additionally, myocyte fractional shortening, muscle tension, and exercise capacity with tafazzin deficiency can be assessed and such defects in muscle function may be reversible, or at least partially reversible, with tafazzin treatment.

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1

Figure 1B:
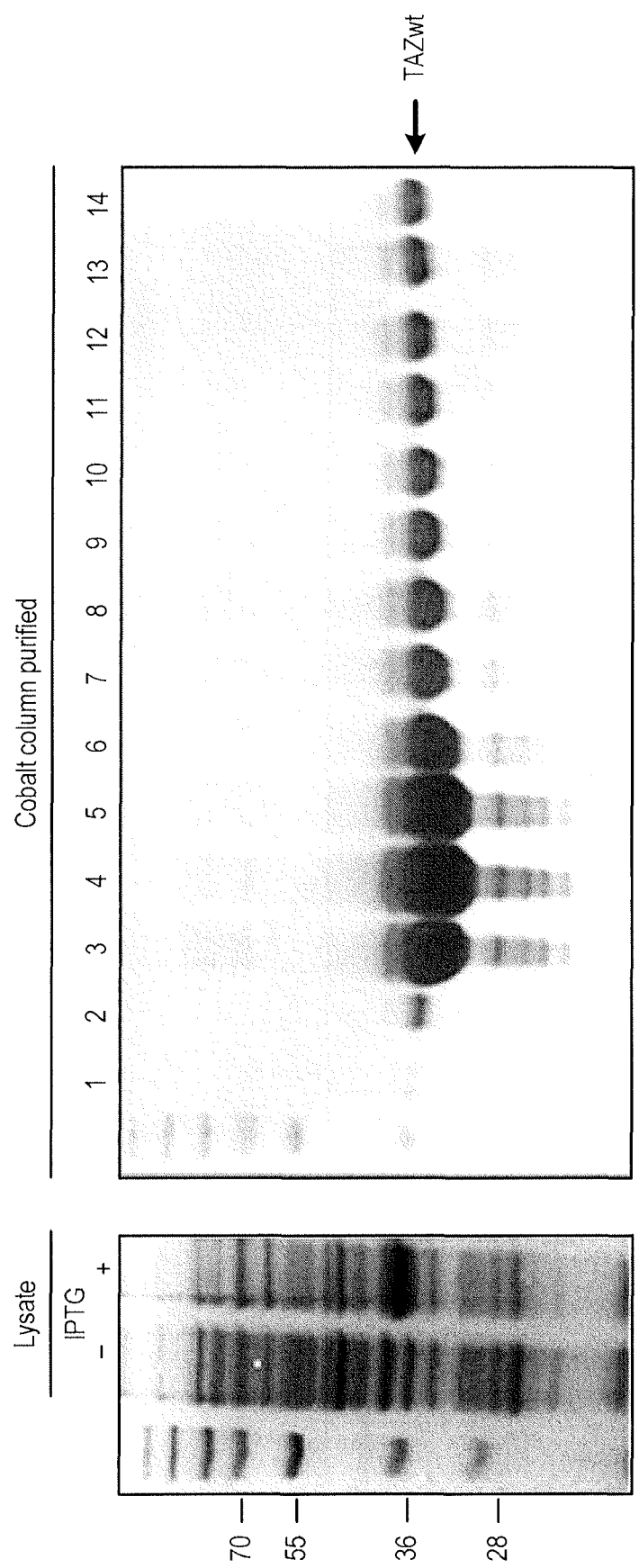
FIG. 1B is an SDS-PAGE of tafazzin (TAZ) wild-type (WT) mouse protein (comprising Antp at the C-terminus) depicting induction in BL21(DE3) cells and purification. Bacterial cells were pre-cultured for 2 hours and subsequently induced with 0.5 mM IPTG for 2 hours. The left panel gel shows pre- (lane 2) and post- (lane 3) induction bacterial lysates. The cells were then lysed and His-tagged tafazzin was purified using a Cobalt (Co) column, as shown in the right panel.

Generation and Assessment of Recombinant Tafazzin Proteins cDNAs for enzymatically active human tafazzin and mouse tafazzin have been cloned into prokaryotic expression plasmids and have generated recombinant tafazzin proteins comprising a *Drosophila* antennapedia tag. Human tafazzin protein and mouse tafazzin protein have also been purified and renatured (see FIGS. 1A and 1B).

Figure 3:
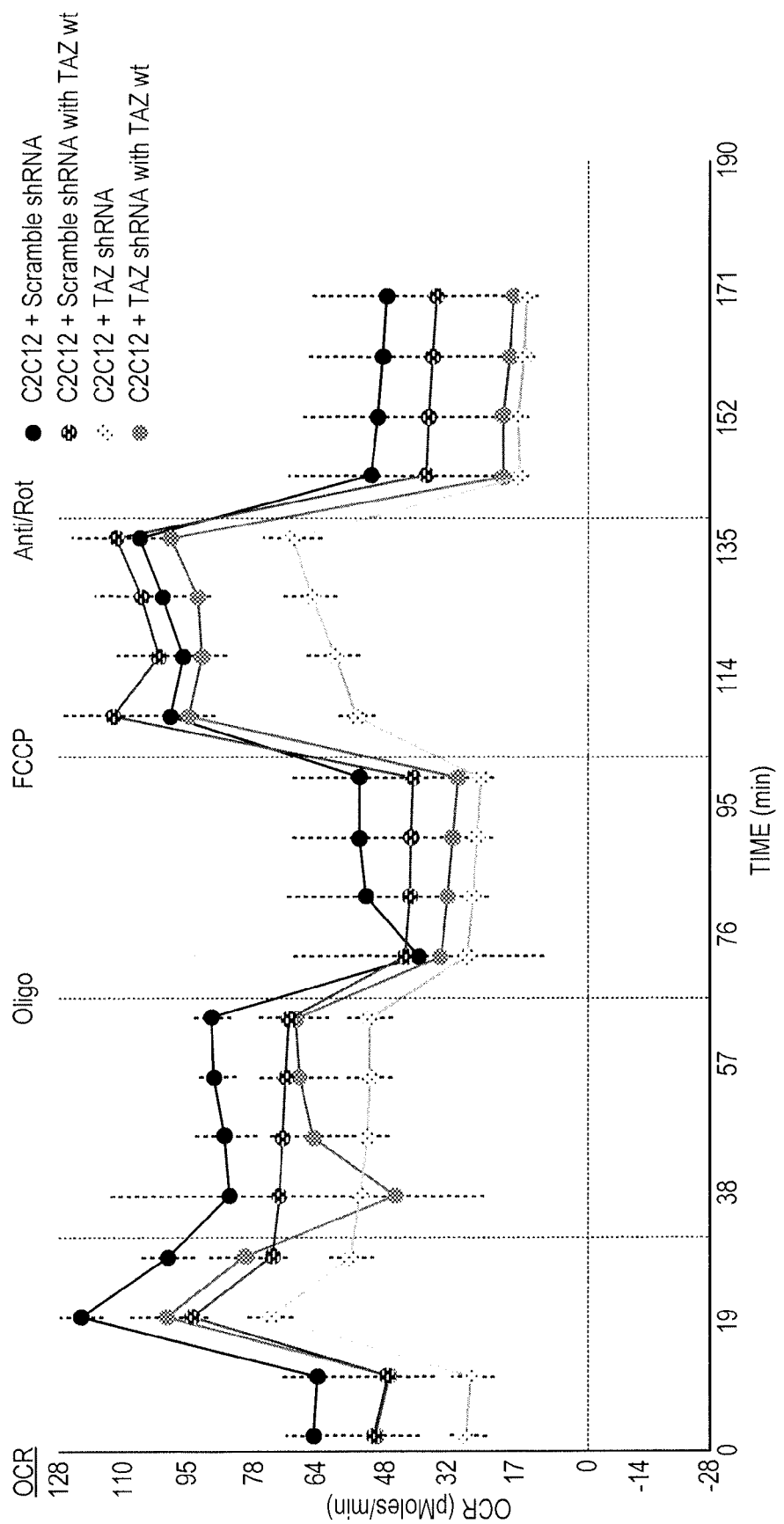
FIG. 3 is a graph depicting oxygen consumption rate (OCR) in C2C12 WT cells or TAZ-knockdown cells after treatment with vehicle control or TAZ-Antp. As depicted, both basal respiration (before oligomycin treatment (Oligo)) and maximal respiration (after FCCP administration) were reduced in TAZ-knockdown cells in comparison to WT cells. Also, as depicted, after treatment with TAZ-Antp, respiration in TAZ-knockdown cells was substantially restored to WT levels.

It has also been found that the antennapedia tag can promote uptake of recombinant tafazzin into a mouse skeletal myoblast cell line. With reference to FIG. 3, the enzymatic activity of delivered protein in C2C12 myoblasts has been assessed by conducting respiration measurements using a Seahorse Bioscience™ instrument to determine the oxygen consumption rate in C2C12 myoblasts, both at baseline and under mitochondrial stress conditions (oligomycin (Oligo) is an ATP synthase inhibitor, FCCP is an electron transport chain accelerator, while rotenone (Rot) interferes with the electron transport chain). FIG. 3 shows the respiration measurements of wild-type and TAZ knockdown 02012 myoblasts after treatment with wild-type mouse tafazzin protein (TAZwt). While wild-type cells treated with wild-type tafazzin show only a slight trend in increase of oxygen consumption, the TAZ knockdown cells demonstrate reduced oxygen consumption at baseline that is rescued to near wild-type levels after treatment with recombinant TAZ. These findings demonstrate that enzyme replacement therapy may be a viable strategy for correcting at least a portion of the metabolic defects in Barth Syndrome.

Example 2

Figure 4:
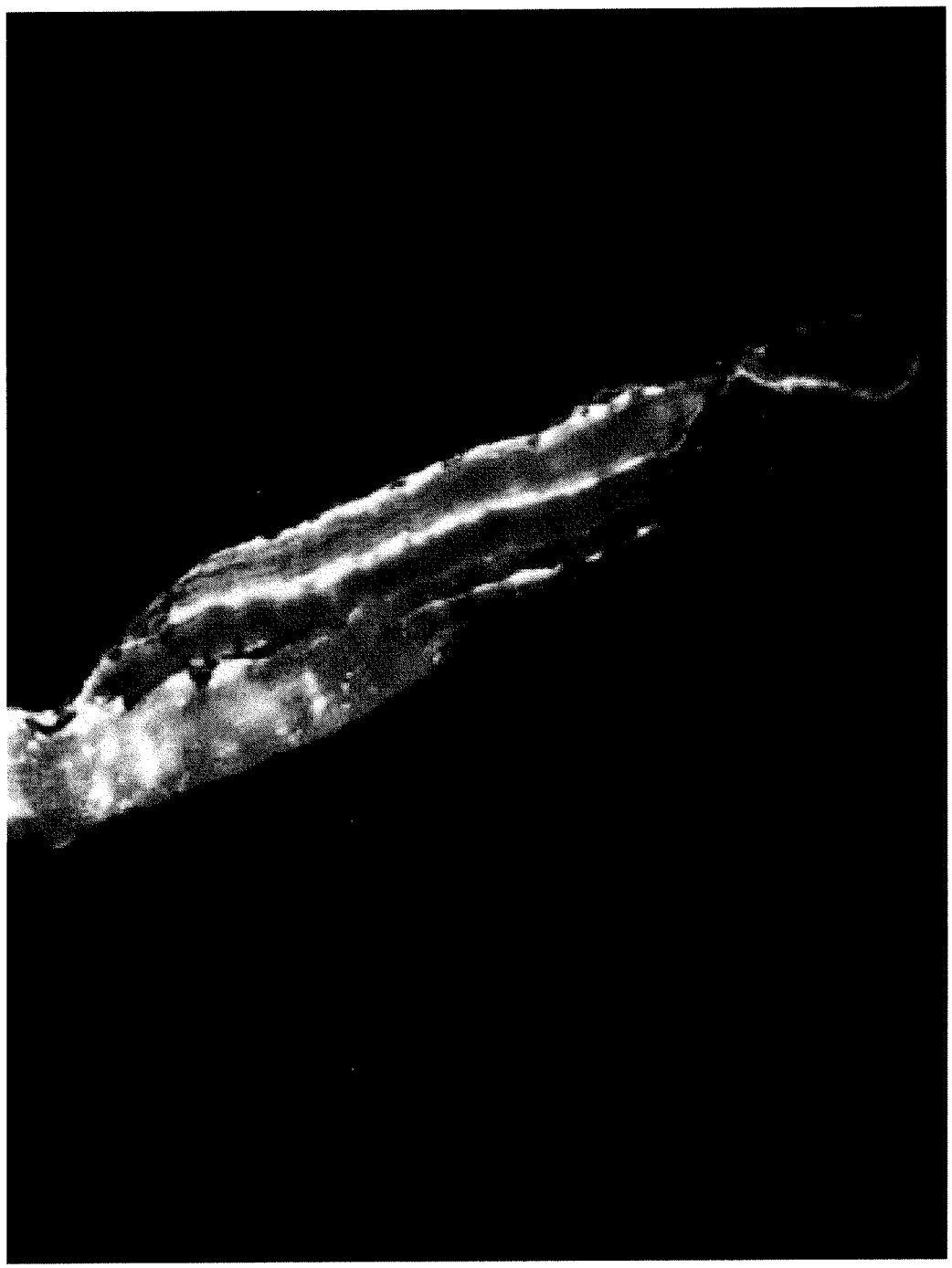
FIG. 4 is a micrograph showing exogenous Cre recombinase engineered for uptake into cells. The Cre recombinase was injected directly into the anterior tibial compartment of an mTmG reporter mouse. Cells undergoing recombination lose expression of the Tomato reporter and gain expression of the eGFP reporter. EDL muscle cryosections were fixed and mounted with DAP/Vectashield®.

Optimization of Delivery of Recombinant Tafazzin Protein to Skeletal Muscle As a step in optimizing protein delivery to skeletal muscle in living mice, an engineered version of Cre recombinase containing an N-terminal polyhistidine-tag and a C-terminal Antp peptide, similar to the recombinant tafazzin protein described above, was developed. This protein was expressed, purified, and renatured using methods similar to those used for tafazzin (data not shown). This protein was subsequently injected into the anterior tibial compartment of an mTmG reporter mouse (see Muzumdar, M. D., et al. (2007) Genesis 45, 593-605). Cells in this mouse are generally red under ultraviolet light at baseline, but uptake of recombinant, enzymatically active Cre recombinase results in excision of the Tomato fluorescent protein gene and activation of GFP, resulting in a green color under ultraviolet light (see FIG. 4).

A technique of ultrasound guided myocardial injection has also been developed (see FIG. 5), which allows or permits microinjection of proteins directly into the heart. This technique has been used to inject Cre directly into the heart of Rosa26LacZ reporter mice (see Mao, X., Fujiwara, Y., and Orkin, S. H. (1999) PNAS 96, 5037-5042) to demonstrate, at least in part, the feasibility of cardiac protein delivery. Uptake of Cre recombinase in the hearts of these mice can activate the LacZ reporter, resulting in a blue color in the presence of the substrate X-gal (see FIG. 6).

Example 3

Assessment of Recombinant Tafazzin Uptake in Skeletal Muscle

Delivery of recombinant tafazzin protein to skeletal muscle deficient for tafazzin can be optimized and recombinant tafazzin protein's effects on contractile function in isolated skeletal muscle cells and fibers can be assessed. It can also be assessed whether skeletal myoblasts deficient in tafazzin show augmented fractional shortening in vitro after tafazzin treatment. Methods can also be developed to treat skeletal muscle in tafazzin-deficient mice with recombinant tafazzin in vitro and by injection in vivo, followed by assessment of uptake, enzymatic activity, and mitochondrial respiration. Additionally, force generation in isolated skeletal muscle fibers can be measured. Recombinant tafazzin may be taken up by intact skeletal muscle and recombinant tafazzin may augment contractile function in muscle cells and skeletal muscle fibers deficient for tafazzin.

Example 4

Generation of C2C12 Myoblasts Deficient for Tafazzin

A lentivirus that overexpresses a validated shRNA (small hairpin RNA or short hairpin RNA) directed against mouse tafazzin has been generated (see Acehan, D., et al. (2011) J. Biol. Chem. 286, 899-908 and Soustek, M. S., et al. (2011) Hum. Gene Ther. 22, 865-871) using an established lentiviral system (see Zhou, B. Y., et al. (2007) Stem Cells 25, 779-789). The lentivirus has been generated and purified by standard methods, C2C12 cells have been infected with the virus, and stable clones have been selected for with puromycin. Tafazzin expression has been measured by qRT-PCR and clones with reduced tafazzin expression and mitochondrial respiration have been identified (see FIG. 3). Cardiolipin isoforms in these cells can be assessed as described (see Phoon, C. K. L., et al. (2012) J Am. Heart Assoc. 1, jah3-e000455-jah000453-e000455) and as discussed below in Example 7.

Example 5

Measurement of Calcium Transients, Calcium Stores, and Fractional Shortening in Skeletal Myoblasts Deficient for Tafazzin after Tafazzin Protein Treatment To determine, at least in part, whether tafazzin treatment rescues contractile function in muscle cells, C2C12 skeletal myoblasts in which tafazzin is knocked down have been generated and can be treated with either tafazzin or vehicle control. Calcium transients can be induced by electrical stimulation at 1 Hz and measured in Fura-2 loaded cells using IonOptix™ equipment as described (see Lindegger N, and Niggli E (2005) J. Physiol. 565, 801-813 and Liu Y, et al. (2012) Am. J. Physiol.-Heart C. 302, H1860-H1870). Cells can be loaded with Fura-2 AM at a concentration of 5 µM for 15 minutes. Ratiometric (360 nm/380 nm) Fura-2 fluorescence can be measured using an IonOptix™ spectrophotometer (Stepper Switch) attached to a fluorescence microscope. Emitted Fura-2 fluorescence can be collected by a 40× objective, passed through a 510 nm filter, and detected by a photomultiplier tube. The velocities and times of $Ca^{2+}$ rise and decay can be calculated. Changes in cell shape over time can be assessed optically using edge detection software, to determine fractional shortening and shortening velocity. Sarcoplasmic reticulum calcium stores can be measured by treatment of Fluo-4 loaded cells with caffeine (10 mM) followed by measurement of the induced to basal fluorescence ratio (F/F0) using a Nikon™ Swept Field confocal system as described (see Zhu W Z, Santana L F, Laflamme M A (2009) PLoS One 4, e5407). Similar studies have been conducted in cardiac myocytes (see Liu Y, et al. (2012) Am. J. Physiol.-Heart C. 302, H1860-H1870).

Example 6

Assessment of Tafazzin-Deficient Skeletal Muscle Function and Rescue of Muscle Dysfunction with Recombinant Tafazzin Transgenic mice containing TAZ-specific shRNA with a Tet-On promoter and a Tet Repressor (TetR), were obtained from The Jackson Laboratory™. In this system, TetR can repress the expression of shRNA under the control of the Tet-On promoter. In the presence of doxycycline, TetR can be inactivated, which can allow or permit the transcription of the shRNA and thus allow or permit the knockdown of tafazzin (see Phoon C K L, et al. (2012) J Am. Heart Assoc. 1, jah3-e000455-jah000453-e0004555; Acehan D, et al. (2011) J. Biol. Chem. 286, 899-908; and Soustek M S, et al. (2011) Hum. Gene Ther. 22, 865-871). Mitochondrial and sarcomeric morphological abnormalities have been noted in the skeletal muscle of 8-month old tafazzin-deficient mice (see Acehan D, et al. (2011) J. Biol. Chem. 286, 899-908), and functional assessment of skeletal muscle can show diminished isometric contractile strength in soleus muscle (see Soustek M S, et al. (2011) Hum. Gene Ther. 22, 865-871). Clinically, Barth syndrome patients may manifest skeletal muscle weakness and exertional fatigue at an early age (see Barth P G, et al. (2004) Am. J. Med. Genet. Part A 126A, 349-354). To determine whether the mice demonstrate skeletal muscle weakness prior to the onset of morphological defects, muscle contractile force and fatigability in 2-month old tafazzin-deficient mice, which reportedly show no structural abnormalities at that age (see Acehan D, et al. (2011) J. Biol. Chem. 286, 899-908), can be assessed.

Force generation and fatigability in isolated mouse extensor digitorum longus (EDL) muscles can be measured as described (see Oishi P E, et al. (2011) J. Vis. Exp. 48). Briefly, EDL muscles can be harvested atraumatically and mounted on a myograph. Twitch tension can be determined by optimizing stimulator voltage and muscle length to achieve maximal tension and a tension vs. time curve can be recorded for a 20% supramaximal stimulus. Tetanic tension can be measured on the same muscle, after a 3 minute rest, by stimulation with a train of supramaximal stimuli for 300 ms at 150 Hz, while recording tension vs. time. The force frequency relationship can be measured by stimulation of the muscle with trains of supramaximal stimuli at 30 Hz, 60 Hz, 100 Hz, 140 Hz, and 160 Hz with 3 minutes rest in between. Percent maximal force can be plotted as a function of frequency. Fatigability can be measured by stimulating the muscle with short trains of tetanic stimuli at 60 Hz for 300 ms, every 3 seconds for 10 minutes. Percent maximal force can be plotted over time. Comparison can be done with EDLs expressing normal, or substantially normal, tafazzin levels.

To determine whether tafazzin treatment augments muscle force, tafazzin protein can be delivered directly to tafazzin-deficient skeletal muscle and effects on force generation can be measured. Enzymatically-active tafazzin can be expressed and purified as shown in FIG. 1. EDL muscles from tafazzin-deficient mice can be isolated and incubated with either tafazzin at a concentration of 1 mg/ml in warmed, oxygenated Krebs solution or vehicle control for 30 minutes. Uptake of tafazzin can be monitored by using fluorescent-tagged protein, while effects on cardiolipin isoforms and muscle tissue mitochondrial respiration can be measured as described below in Examples 7 and 8. Twitch tension, tetanic tension, force frequency relationships, and fatigability can also be measured as described above.

Figure 2:
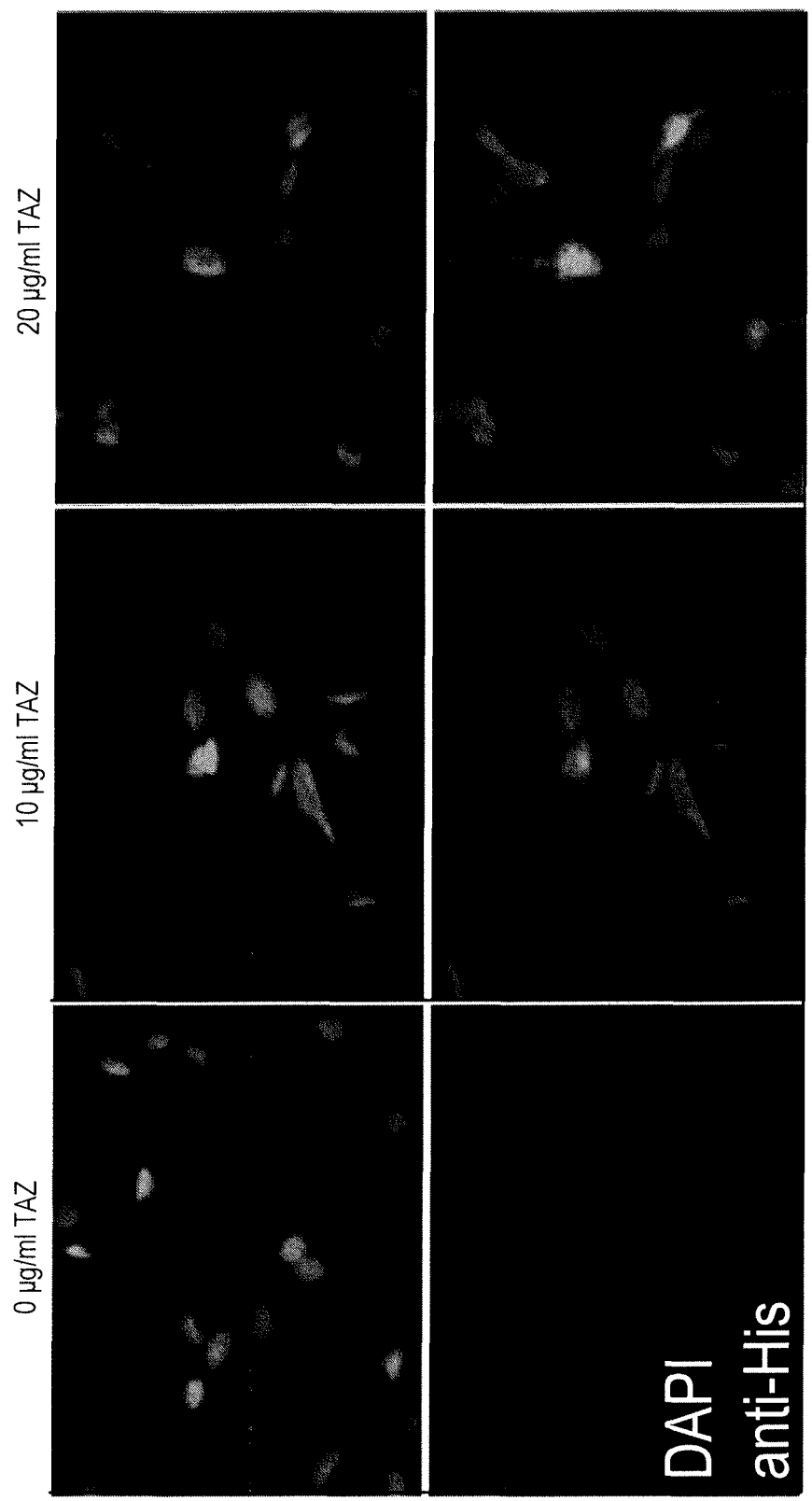
FIG. 2 depicts tafazzin (TAZ) wild-type mouse protein (comprising Antp at the C-terminus) delivery to undifferentiated C2C12 cells. Cells were incubated with 10% FBS/DMEM and either 0 μg/ml, 10 μg/ml, or 20 μg/ml of protein for 24 hours, then fixed with 2% PFA and stained with Alexa Fluor 555-conjugated anti His tag. Cells were then mounted with Vectashield® comprising DAPI.

Additionally, it can also be assessed whether tafazzin protein directly injected into the anterior tibial compartment surrounding the mouse EDL muscle rescues function. Recombinant tafazzin in pluronic gel can be injected directly into the anterior tibial compartment at varying dosages. Single injections of enzymatically active tafazzin can be performed at doses of 0 µg (vehicle control), 10 µg, 50 µg, and 100 µg. Additionally, muscles can be harvested at 6 hours, 12 hours, 24 hours, and 48 hours after injection for immunofluorescent analysis of protein uptake as shown in FIG. 2. Twitch tension, tetanic tension, force-frequency, and fatigability can be measured after verification of protein uptake, as previously described (see Oishi P E, (2011) J. Vis. Exp. 48 and Stone, A V, et al. (2011) J. Orthop. Res. 29, 1764-1770) and as discussed above.

Example 7

Assessment of Tafazzin Activity in Cultured Skeletal Myoblast Cells

Tafazzin can promote the formation of tetralinoleoyl cardiolipin over monocardiolipin, and the relative preponderance of cardiolipin derivatives can indicate, or reflect, overall tafazzin activity. Cardiolipin isoforms in C2C12 tafazzin knockdown cells, with and without recombinant tafazzin treatment, can be quantified. To do so, phospholipids can be extracted from lyophilized cells. The cells can be resuspended in 1 ml demineralized water, followed by the addition of 3 ml chloroform-methanol (2:1, v/v) and an internal standard (0.4 nmol of tetramyristoyl-cardiolipin, Avanti® Polar Lipids, Inc., Alabaster, Ala.). After about 20 minutes of sonication in a sonicator bath, the mixture can be cooled on ice for about 15 minutes and centrifuged for about 10 minutes at 1000 g. The lower phase can be transferred to another tube and the upper phase can be reextracted with 3 ml chloroform-methanol (2:1, v/v). The combined organic phases can be dried and dissolved in 150 µl chloroform/methanol/water (50:45:5, by volume), comprising 0.01% ammonia. An aliquot of 10 µl can be used for high performance-liquid-chromatography (HPLC) mass spectrometry as described previously (see Houtkooper R H, et al. (2006)

FEBS Lett. 580, 3059-3064). The ratio of monolysocardiolipin over cardiolipin can be calculated from the areas under the curve of the HPLC profiles of the complete mass spectra (see Kulik W, et al. (2008) Clin. Chem. 54, 371-378).

Example 8

Assessment of Mitochondrial Respiration and Respiratory Complex Activity in Skeletal Myoblast Cells Deficient for Tafazzin Before and after Tafazzin Protein Treatment Mitochondrial respiration in saponin-permeabilized C2C12 cells expressing variable amounts of tafazzin, as previously described (see Saks V A, et al. (1998) Mol. Cell Biochem. 184, 81-100), and as shown in FIG. 3, can be measured using a Seahorse Laboratories™ bioanalyzer. These results can be confirmed and more careful measurements can be generated using a respirometry chamber (Oxygraph-2k, Oroboros Instruments™, Austria) to measure baseline respiration. To measure the activities of various complexes within the respiratory chain, a previously described protocol can be used (see N'Guessan B, et al. (2004) Mol. Cell Biochem. 256-257, 267-280). Briefly, overall respiration due to activity of complexes I, II, III, and IV can be assessed by addition of saturating amounts of ADP in the presence of glutamate and malate. Rotenone and succinate can subsequently be added to inhibit complex I and facilitate respiration by complexes II, III, and IV. Respiration due to complex IV can be assessed after the subsequent addition of antimycin to inhibit complex III and addition of TMPD-ascorbate as the appropriate substrate to fuel complex IV.

Skeletal myoblasts deficient for tafazzin may have diminished fractional shortening when compared to myoblasts expressing normal levels of tafazzin. Calcium transients and calcium stores may not be affected, as a consequence of tafazzin deficiency may be a change in mitochondrial respiration, which can alter cellular ATP stores (see He Q (2010) Am. J. Physiol.-Heart C. 299, H210-H216). The skeletal myoblasts may also take up tafazzin and recombinant, enzymatically-active tafazzin may promote formation of tetralinoleoyl cardiolipin, improve mitochondrial respiration, and rescue any observed defects in fractional shortening in the tafazzin deficient cells. Isolated EDL muscles from tafazzin-deficient mice may also show diminished twitch tension, tetanic tension, force-frequency, and increased fatigability, and treatment of these muscles ex vivo with recombinant tafazzin may improve these contractile properties. Direct injection of tafazzin protein into the anterior tibial compartment may also promote uptake into tafazzin-deficient EDL muscle in vivo and may augment force generation in isolated EDL muscles.

In some embodiments, the recombinant tafazzin may enter the muscle but may not rescue contractile defects. In some such embodiments, it could be assessed whether the exogenous tafazzin altered the cardiolipin profile within the explanted EDL muscle and whether it improved mitochondrial respiration. In certain embodiments, if there is no, or little, shift towards the tetralinoleoyl form or no, or little, improvement in mitochondrial respiration, a longer term rescue strategy could be tested using multiple injections of tafazzin protein at weekly intervals over several weeks.

Example 9

Optimization of Delivery of Recombinant Tafazzin Protein to Adult Cardiac Myocytes Deficient for Tafazzin and Assessment of Effects on Contractile Function Adult cardiac myocytes can be isolated from mice deficient in tafazzin and treatment with recombinant tafazzin may be optimized, as measured by uptake, enzymatic activity, and mitochondrial respiration. Calcium transients, fractional shortening, shortening velocity, and relaxation velocity with and without tafazzin treatment can be compared. Recombinant tafazzin may be taken up by adult cardiac myocytes and may improve fractional shortening in tafazzin-deficient cells.

Example 10

Isolation of Adult Mouse Cardiomyocytes from Tafazzin Knockdown Mice and Assessment of Tafazzin Uptake Tafazzin knockdown can be induced in inducible tafazzin knockdown mice during gestation using doxycycline as described (see Acehan D, et al. (2011) J. Biol. Chem. 286, 899-908). Adult cardiomyocytes can be isolated as previously described (see Liu Y, et al. (2012) Am. J. Physiol.-Heart C. 302, H1860-H1870; Xiang F, et al. (2006) Am. J. Physiol.-Heart C. 290, H1997-H2006; Sambrano G R, et al. (2002) Nature 420, 712-714). Hearts from 8-week old mice can be removed, perfused with enzyme solution to promote dispersion, and adult myocytes can be isolated according to the Alliance for Cell Signaling protocol.

The tafazzin-deficient cells can then be treated with enzymatically active tafazzin and the purified protein can be mixed in with the cell culture media (10% fetal bovine serum DMEM). Zhou, et al. (see (2007) Stem Cells 25, 779-789) found that proteins conjugated with a permeability peptide were able to enter cells at concentrations ranging from 0.5 µg/ml to 8 µg/ml within 6 hours and that these transduced proteins were stable inside the cells for up to 48 hours. Plated cells can be treated with 0 µg/ml, 5 µg/ml, 10 µg/ml, 15 µg/ml, 20 µg/ml, and 25 µg/ml for a duration ranging between 6 hours to 48 hours. Uptake can be measured by immunofluorescence as shown in FIG. 2.

Example 11

Assessment of Contractile Function, Mitochondrial Respiration and Respiratory Complex Activity in Adult Myocytes Deficient for Tafazzin Before and after Tafazzin Protein Treatment Changes in cell shape over time, reflecting, at least in part, the contractile function of the isolated cardiomyocytes, can be assessed optically using IonOptix™ video microscopy with edge detection software, to determine fractional shortening, shortening velocity, and relaxation velocity of both control and TAZ-deficient cardiomyocytes, as has been done previously (see Valianpour F, et al. (2002) J. Pediatr. 141, 729-733), before and after treatment with purified TAZ.

The effects of tafazzin delivery can be tested using a high throughput metabolic analyzer (Seahorse Biosciences™) or an oxygraph (Oroboros™) to assess changes in total oxygen consumption rate in mitochondria, both at baseline and after treatment, as described above. Likewise, the ratio of CL molecular species can be measured using mass spectrometry, as described above.

Adult myocytes from tafazzin-deficient animals may demonstrate decreased fractional shortening and shortening velocity. Adult myocytes from tafazzin-deficient animals may also demonstrate impaired relaxation velocity. Treatment of tafazzin-deficient adult cardiac myocytes with enzymatically active tafazzin protein engineered for cellular uptake may lead to increased mitochondrial respiration, possibly by increasing the activity of complex III+IV, and may lead to increased predominance of tetralinoleoyl cardiolipin over monocardiolipin. Tafazzin treatment may also improve fractional shortening and relaxation.

Example 12

Determine Whether Recombinant Tafazzin Improves Exercise Capacity and Cardiac Function after Local and Systemic Delivery in Mice Deficient for Tafazzin Skeletal and cardiac muscle in tafazzin-deficient mice can be treated with recombinant tafazzin by direct injection in vivo and systemically through retroorbital injection. Uptake into heart and skeletal muscle can be assessed followed by measurement of exercise capacity and/or cardiac function in treated animals. Administration of recombinant tafazzin may improve exercise capacity and cardiac function in tafazzin-deficient mice.

Example 13

Skeletal Muscle Function During Exercise in Tafazzin Knockdown Mice after Tafazzin Replacement Therapy A baseline physiological assessment of skeletal muscle function in tafazzin knockdown mice can be performed and it can be determined whether locally or systemically administered tafazzin protein can rescue skeletal muscle dysfunction. Voluntary wheel running can be assessed and enforced treadmill running in tafazzin-deficient mice can be measured as described (see McCullagh, K J, et al. (2008) Mamm. Genome 19, 339-351). Enzymatically active tafazzin protein can be administered into the anterior tibial compartment as described above and as shown in FIG. 4. Protein can also be injected retroorbitally in doses of about 100 µg daily for four days and uptake into muscle on day 5, day 6, and day 7 can be measured by immunofluorescence of excised muscle and by Western blotting of skeletal muscle. Cardiolipin isoforms, mitochondrial respiration, and EDL muscle mechanics can also be assessed as described above. Once uptake is verified, voluntary wheel running can be assessed by placing individual mice in cages with monitored wheels during the peri-injection period to allow them to become acclimated for a total of 7 days after the first injection. The total number of revolutions can then be quantified over the ensuing 7 days using ClockLab software (Actimetrics™). Exercise capacity can also be assessed by subjecting tafazzin-deficient mice to a graded treadmill exercise protocol before and after tafazzin injection. Untrained mice can run on a computerized treadmill for 10 minutes per day at 10 m/min to 14 m/min for 5 days prior to tafazzin injection. Mice can then have a baseline study in which they undergo graded exercise challenge beginning at 14 m/min for 2 minutes, increasing by 2 m/min for another 2 minutes up until a maximum speed of 30 m/min, all at a 6 degree incline. The treadmill can log interruptions in running time, which may reflect inability to perform. After retroorbital injection of recombinant tafazzin over 4 days, the mice can again undergo acclimation to the treadmill by running at 10 m/min to 14 m/min on day 5, day 6, and day 7. On day 8, the mice can undergo graded exercise challenge again and the results can be compared with the baseline study.

Example 14

Figure 5:
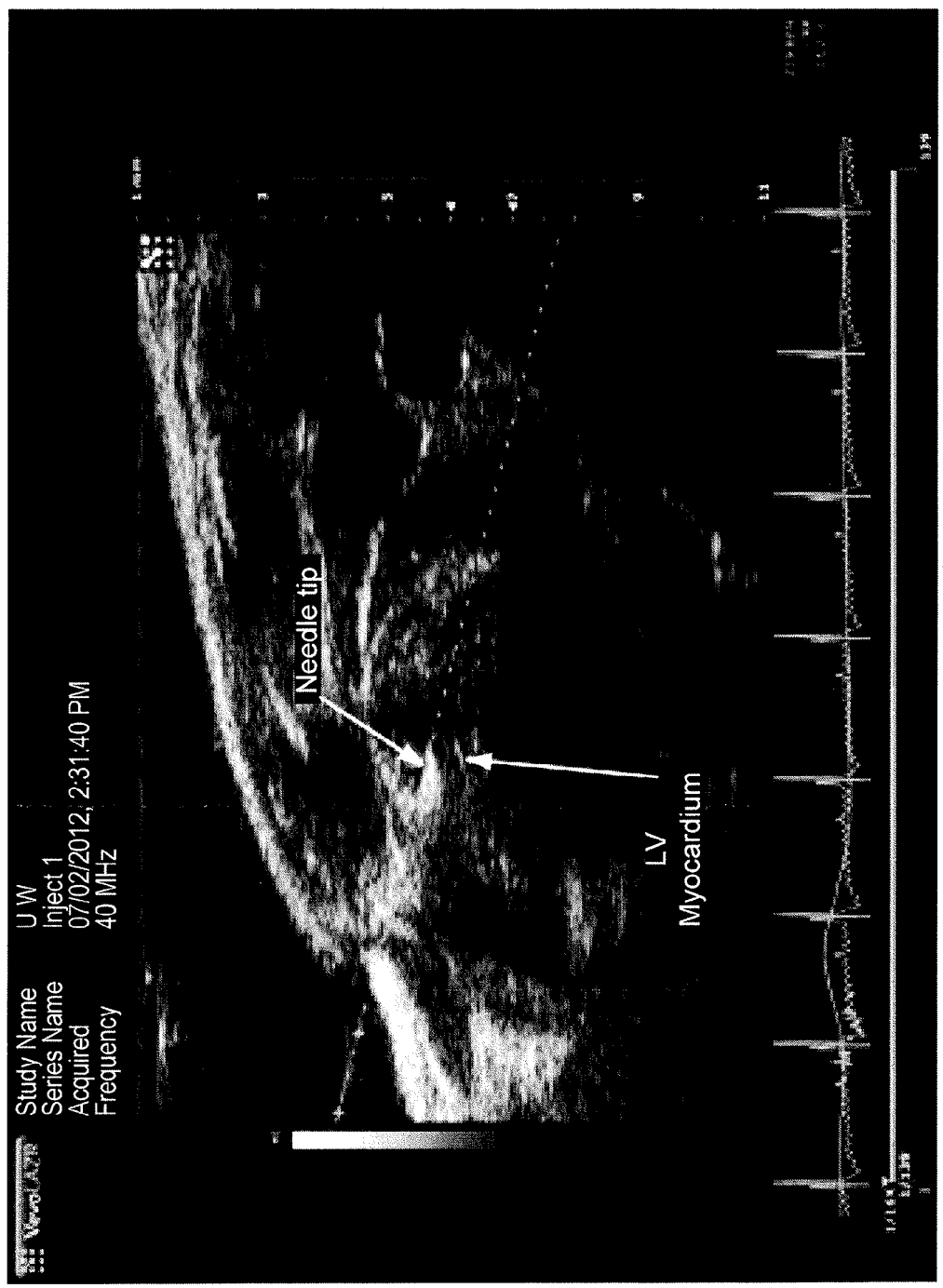
FIG. 5 depicts ultrasound guided closed chest microinjection of contrast into ventricular myocardium through the chest wall and into beating left ventricular myocardium using a Hamilton syringe with a 29 gauge needle.
Figure 6:
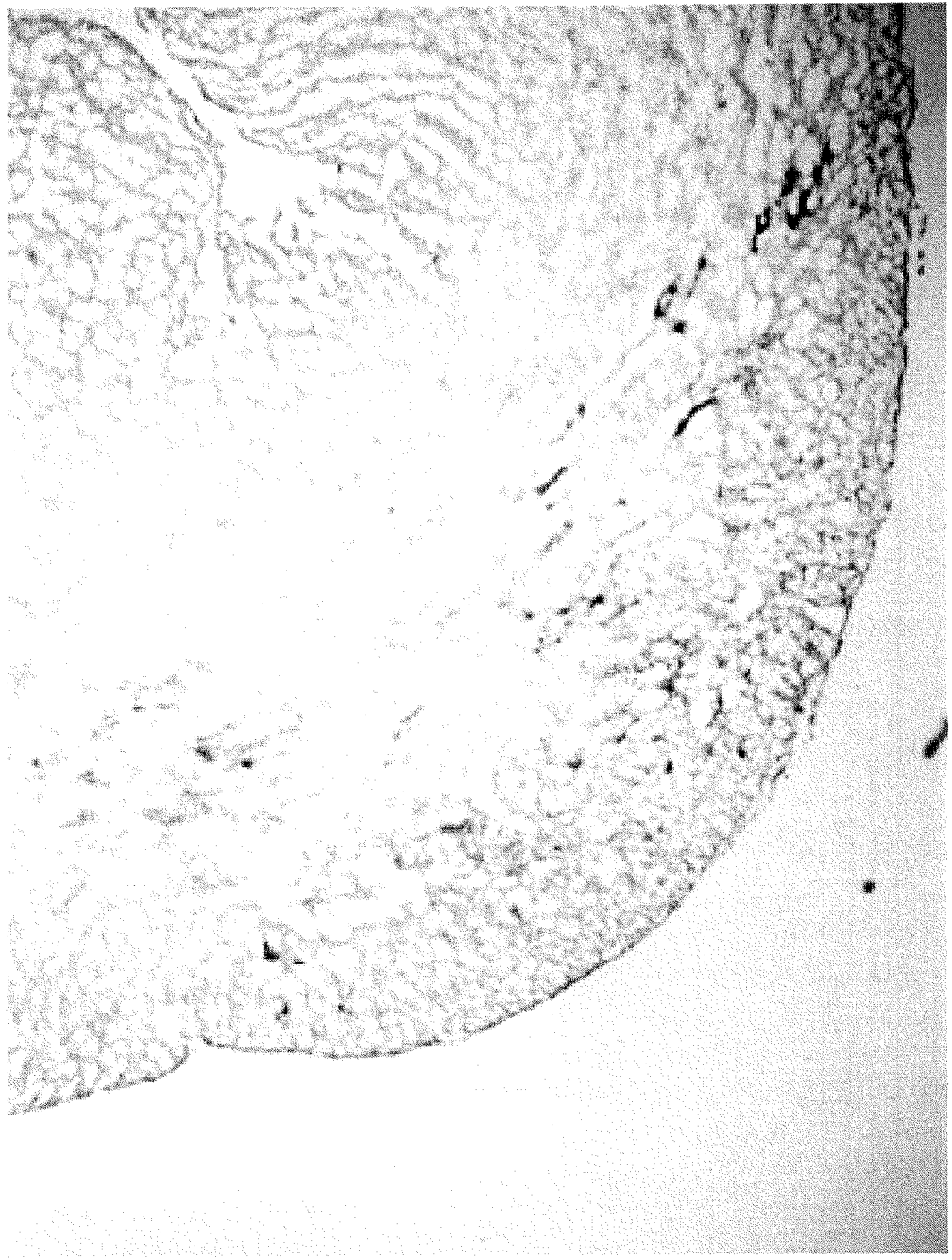
FIG. 6 is a cryosection of left ventricular myocardium, fixed, and stained with X-gal. Exogenous Cre recombinase was injected into the heart under ultrasound guidance to activate a Rosa26 LacZ reporter. Cre recombinase with a cellular permeability tag in pluronic gel was injected directly into the left ventricular myocardium. The heart was harvested at day 4 post injection.

Cardiac Muscle Function in Tafazzin Knockdown Mice after Tafazzin Replacement Therapy Tafazzin-deficient mice reportedly develop diastolic dysfunction early (see Phoon, C K L, et al. (2012) J Am. Heart Assoc. 1, jah3-e000455-jah000453-e000455) and systolic dysfunction relatively late (see Acehan D, et al. (2011) J. Biol. Chem. 286, 899-908 and Soustek M S, et al. (2011) Hum. Gene Ther. 22, 865-871). Enzymatically active tafazzin can be administered using ultrasound guided injection directly into the myocardium as shown in FIGS. 5 and 6. Tafazzin can also be administered systemically by retroorbital injection as described above. The effects of tafazzin on diastolic dysfunction in young mice (6 weeks to 8 weeks) can be assessed using echocardiography. Effects of tafazzin on systolic dysfunction in older mice (8 months) can also be assessed using echocardiography. Uptake into myocardium, effects on cardiolipin metabolism, and mitochondrial respiration can be assessed as described above.

Local and systemic administration of tafazzin to tafazzin-deficient mice may lead to uptake into skeletal muscle, improved cardiolipin modification, improved mitochondrial respiration, and improved exercise performance. Local and systemic administration of tafazzin may also improve diastolic and systolic dysfunction in tafazzin-deficient hearts.

Example 15

Figure 7A:
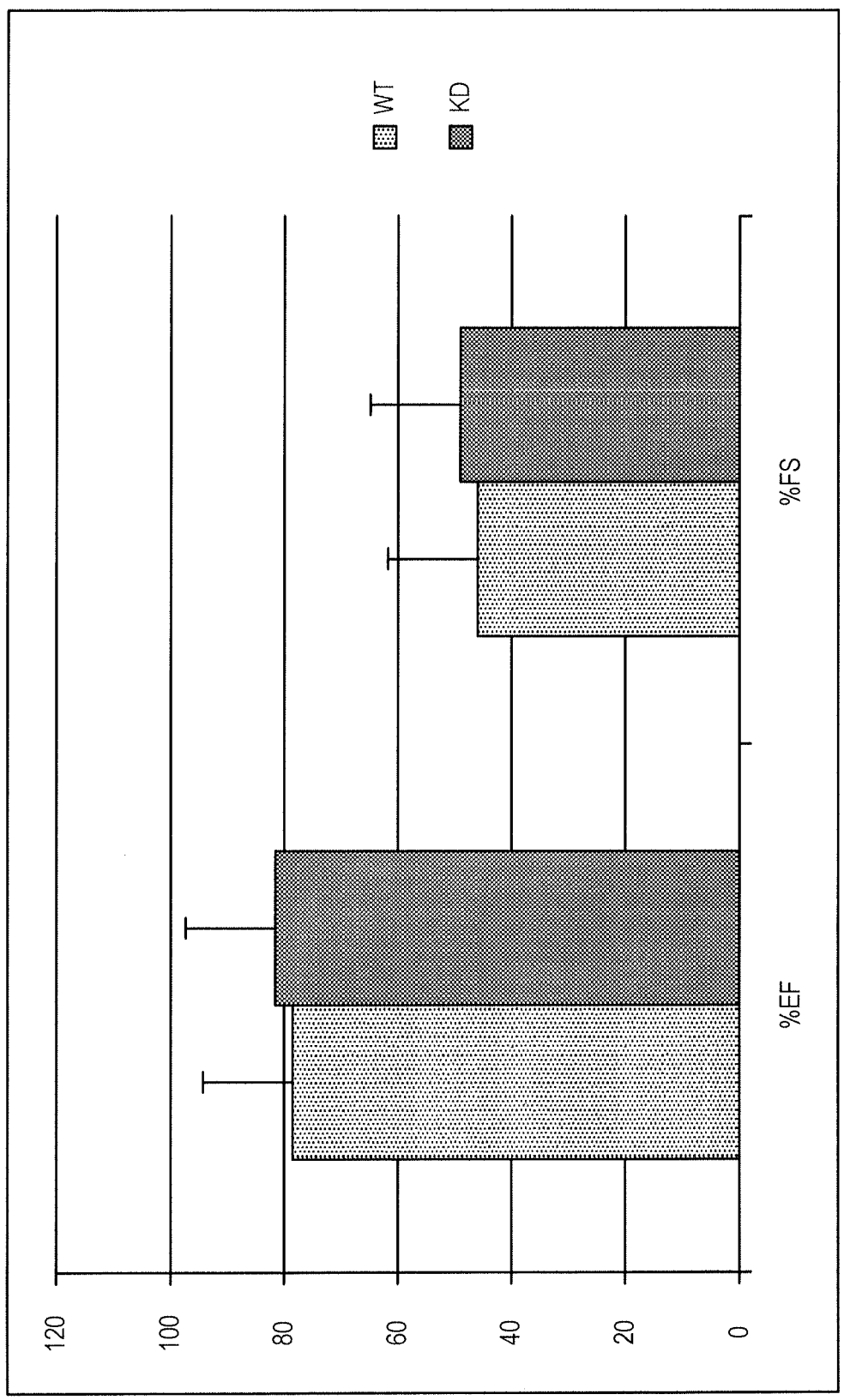
FIG. 7A is a graph depicting ejection fraction (% EF) and fractional shortening (% FS) in wild-type (WT) and TAZ-knockdown (KD) mice at 8 weeks of age.
Figure 7B:
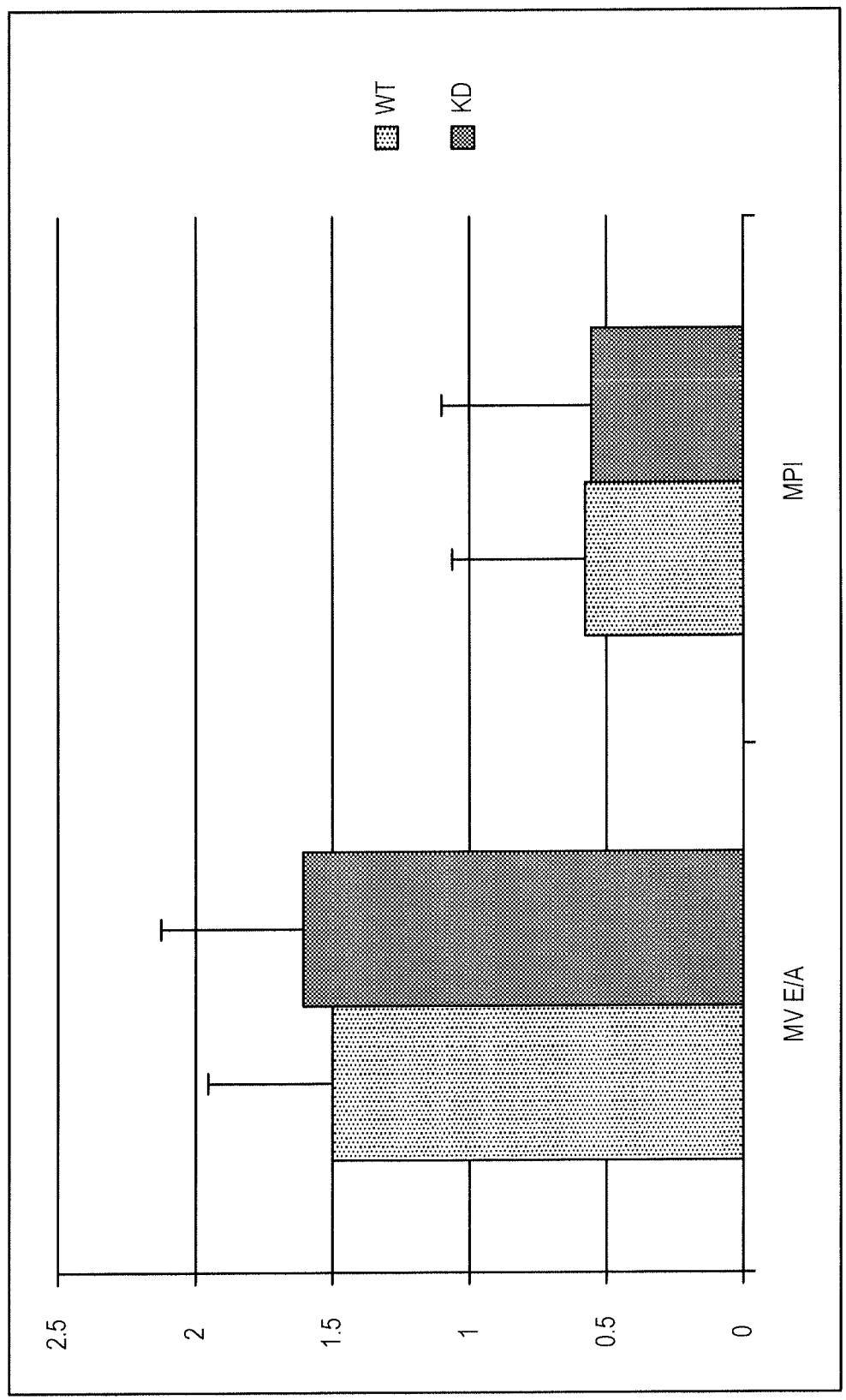
FIG. 7B is a graph depicting E/A ratio (MV E/A) and myocardial performance index (MPI) in wild-type (WT) and TAZ-knockdown (KD) mice at 8 weeks of age.

Mice Deficient in TAZ have Normal Ventricular Function at Baseline and Isolated Myocytes have Normal Fractional Shortening and Relaxation Time Doxycycline-inducible TAZ-knockdown mice were obtained from The Jackson Laboratory™ and females were fed with doxycycline chow (625 mg/kg) prior to mating so that offspring would have induction of shRNA directed against TAZ from the time of conception. These offspring were then raised to the age of 8 weeks and baseline echocardiography was performed. As shown in FIGS. 7A and 7B, no difference, or substantially no difference, was observed in baseline fractional shortening, ejection fraction, E/A ratio, or myocardial performance index. To determine whether TAZ-KD hearts exhibit any defects at the myocyte level, adult cardiac myocytes were isolated from 8-week old TAZ-KD mice and fractional shortening, calcium transient, and diastolic relaxation was assessed using an IonOptix™ Myocyte Calcium Photometry and Contractility system as has been done previously (see Liu Y, et al. (2012) Am. J. Physiol.-Heart C. 302(9), H1860-H1870). As shown in Table 1, adult myocytes from 2-month old TAZ-KD mice are longer, but have similar fractional shortening, sarcomere length, and calcium transients when compared with WT myocytes. The units in Table 1 are micrometers (µm).

TABLE 1

Adult Cardiomyocyte IonOptix ™ Data from WT and TAZ-KD Mice

| | cell length | | | sarcomere length | | fura-2 | |
|---|---|---|---|---|---|---|---|
| | baseline | peak | FS | baseline | peak | baseline | peak |
| WT | 123.944 | 116.776 | 0.058 | 1.706 | 1.565 | 1.268 | 1.384 |
| KD | 133.213 | 127.473 | 0.043 | 1.743 | 1.640 | 1.244 | 1.352 |
| p-val | 0.009 | 0.064 | 0.486 | 0.659 | 0.641 | 0.829 | 0.809 |

Figure 8:
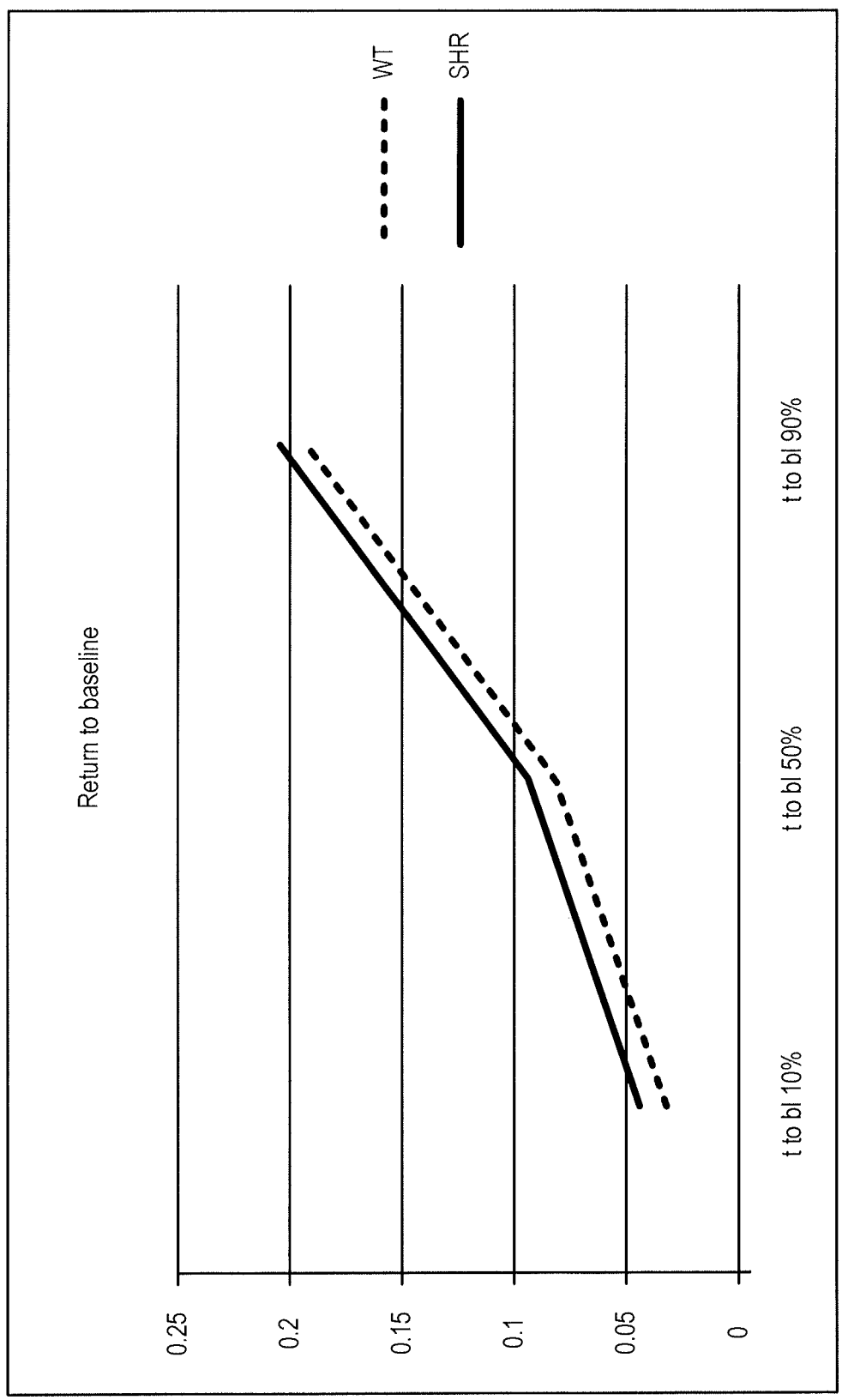
FIG. 8 is a graph depicting relaxation in adult cardiomyocytes isolated from 2-month old wild-type (WT) and TAZ-knockdown (SHR) mice.

FIG. 8 demonstrates that the kinetics of relaxation are nearly identical, or substantially identical, in WT and knock-down cells, indicating that diastolic relaxation may not be impaired at the cellular level. Previous reports have indicated that systolic dysfunction does not appear until about 8-months of age in these mice when maintained on doxycycline-containing chow (Acehan D, et al. (2011) J. Biol. Chem. 286, 899-908 and Soustek M S, et al. (2011) Hum. Gene Ther. 22, 865-871).

Example 16

Recombinant Tafazzins Tethered to Cell-Penetrating Peptides Enter Cells and Localize to Mitochondria To develop a potential treatment for TAZ deficiency, recombinant tafazzin proteins were engineered comprising a short peptide at the C-terminus, either derived from the *Drosophila* antennapedia protein (Antp), which has been shown to promote uptake of proteins into cells (Rapoport M, et al. (2008) Mol. Ther. 16, 691-697; Schwarze S R, Hruska K A, Dowdy S F. (2000) Trends Cell Biol. 10, 290-295; and Zhou H, et al. (2009) Cell Stem Cell 4, 381-384), or a cardiac targeting peptide (CTP) (Zahid M, et al. (2010) PLoS One 5, e12252). The antennapedia peptide has been shown to facilitate entry of proteins into cells through a mechanism that may involve interactions with highly cationic basic residues (Schwarze S R, Hruska K A, Dowdy S F. (2000) Trends Cell Biol. 10, 290-295).

Figure 9:
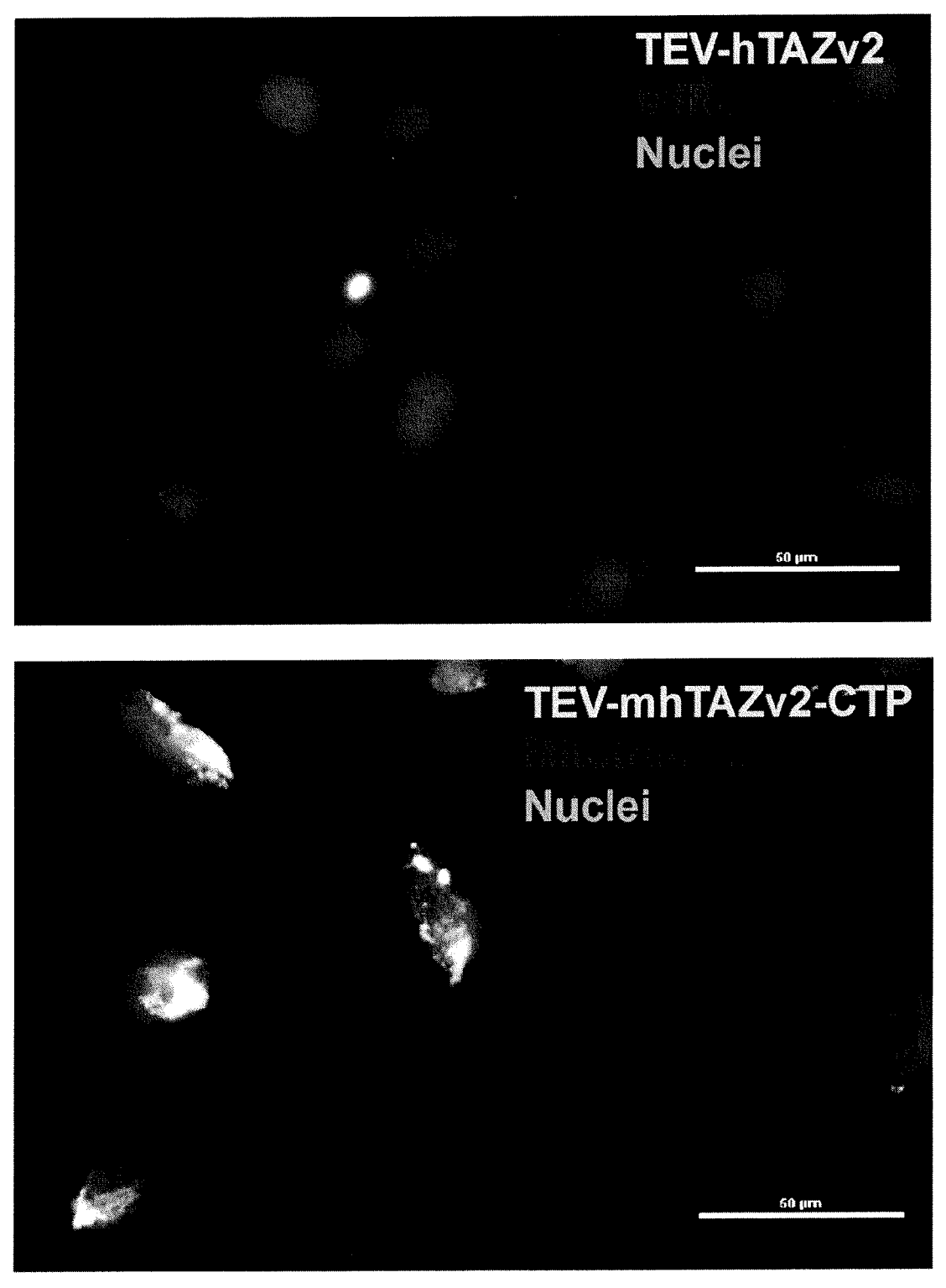

As discussed above, the recombinant tafazzin has been induced and purified using *E. coli* (see FIG. 1) and the ability of the recombinant protein to enter H9c2 myoblasts has been tested. It was found that CTP-tagged TAZ protein successfully enters the cells and colocalizes with mitochondria, while TAZ lacking CTP does not enter the cell (see FIG. 9). The association of TAZ-Antp with the mitochondrial fraction after treatment was analyzed and it was found that it copurifies with mitochondria (data not shown).

Example 17

Recombinant Tafazzin Rescues Defective Mitochondrial Respiration in Tafazzin-Deficient Cells To determine whether the recombinant protein can rescue defective mitochondrial respiration, mitochondrial respiration measurements were conducted using a Seahorse Biosciences™ Extracellular Flux Analyzer to determine the oxygen consumption rate in both WT and C2C12 myoblasts in which TAZ is knocked down by a lentiviral shRNA construct and in which palmitate is used as a substrate. Measurements were conducted both at baseline and under mitochondrial stress conditions using: oligomycin, an ATP synthase inhibitor; FCCP, an electron transport chain accelerator; and rotenone, which blocks mitochondrial respiration. FIG. 3 shows the respiration measurements of wild-type C2C12 myoblasts, as well as TAZ knock down C2C12 cells, with or without treatment with wild-type tafazzin protein tagged with Antp peptide.

TAZ knockdown cells show a marked decrease in baseline and maximal oxygen consumption as compared to the wild-type cells, which is consistent with data from BTHS patient-derived fibroblasts (see Houtkooper R H, et al. (2009) Biochim. Biophys. Acta 1788, 2003-2014), lymphocytes, and cardiomyocytes isolated from a BTHS mouse model. While WT cells treated with tafazzin show only a slight trend in increase of oxygen consumption during maximal respiration, the TAZ deficient cells are rescued to essentially WT oxygen consumption levels. These results indicate that the protein is able to reach the mitochondria, where it is enzymatically active and able to restore respiration. A similar analysis done in primary neonatal cardiomyocytes isolated from TAZ-KD mice comparing TAZ-AntP and TAZ-CTP, and using glucose as a substrate, showed that both proteins could augment respiration in both TAZ-KD and WT cells (data not shown), with TAZ-CTP giving slightly better results in WT cells.

Example 18

Figure 10:
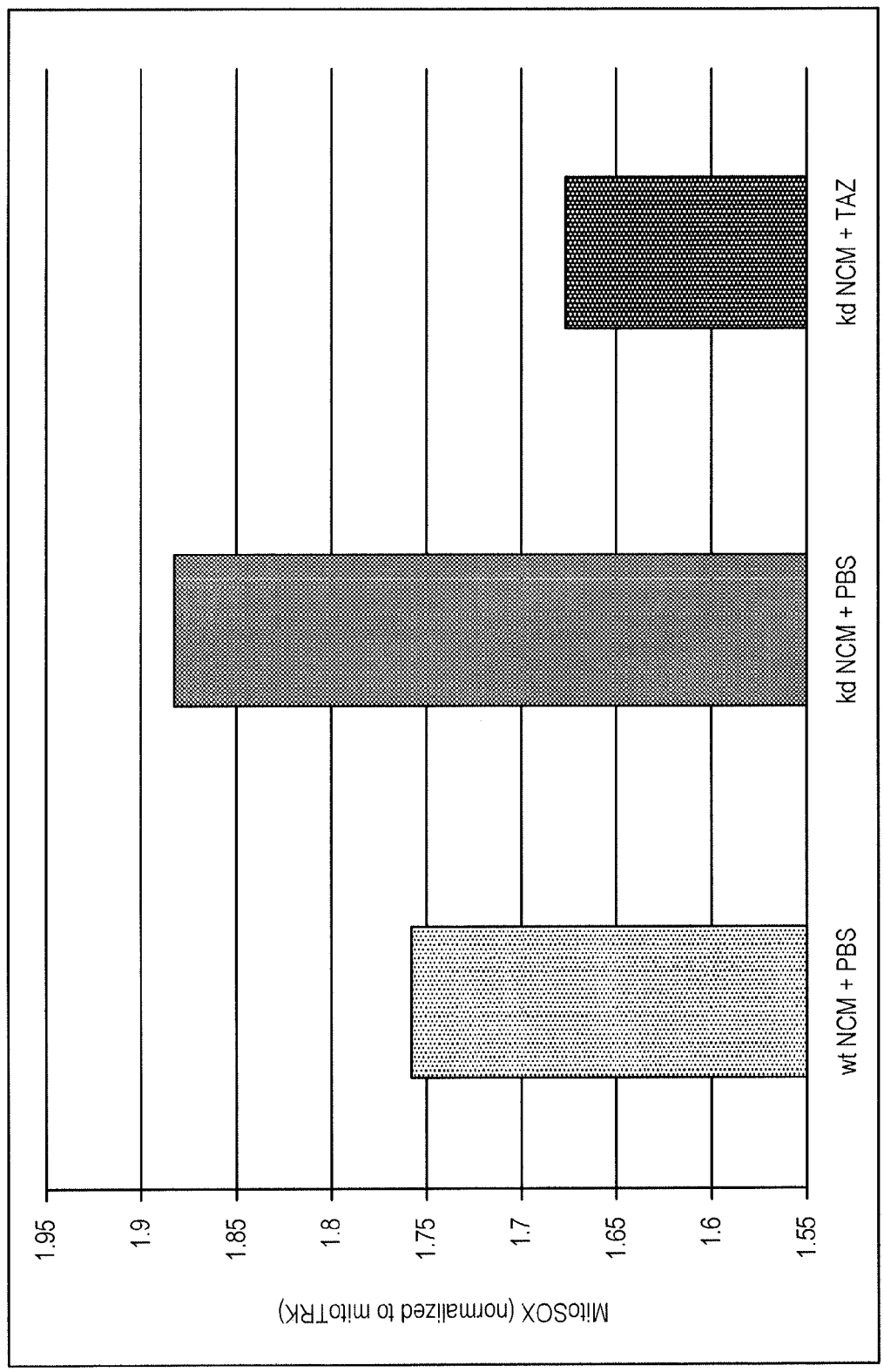
FIG. 10 is a graph depicting ROS levels in WT and TAZ-KD neonatal cardiomyocytes (NCM) at baseline and after TAZ-Antp treatment.

Tafazzin-Deficient Neonatal Cardiomyocytes Demonstrate Increased Amounts of ROS that can be Suppressed by Recombinant Tafazzin To determine whether tafazzin-deficiency leads to increased ROS generation in cardiomyocytes, neonatal cardiomyocytes were isolated from TAZ-KD and WT littermates and ROS levels were measured with MitoSOX Red and total mitochondria was measured with MitoTracker Green FM staining according to the manufacturer's instructions (Life Technologies™). As shown in FIG. 10, ROS levels normalized to total mitochondria are increased in TAZ-KD cells. Treatment with TAZ-Antp suppresses ROS levels to those comparable to WT cells.

Example 19

Recombinant Tafazzin can be Delivered Directly to the Heart

Figure 11:
FIG. 11 is a micrograph depicting TAZ-CTP uptake into the myocardium.
Figure 12A:
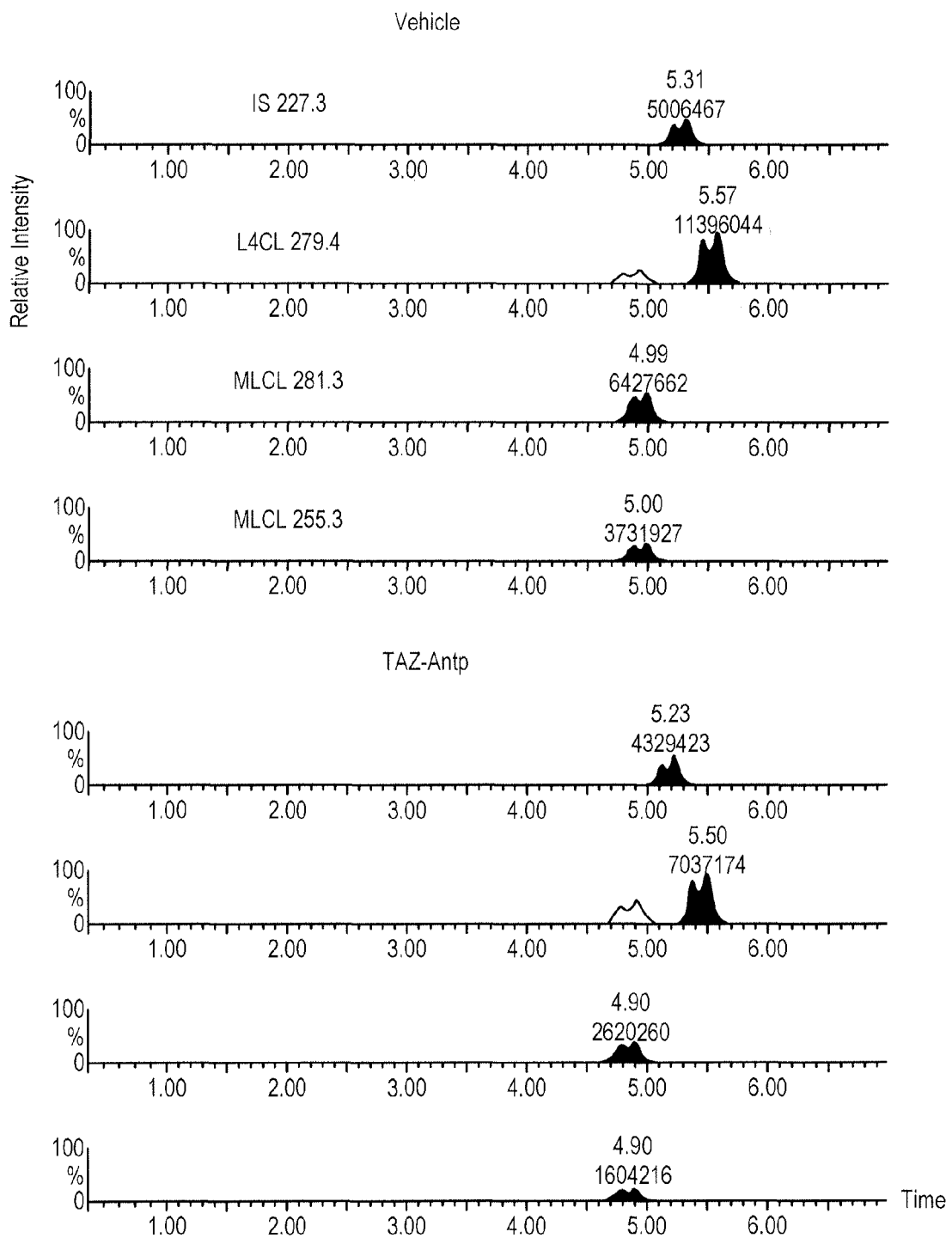
FIG. 12A is a series of multiple reaction monitoring (MRM) chromatograms for monolysocardiolipin (MLCL, sum of m/z 582.9→m/z 281.3 and m/z 582.9→m/z 255.3) and tetralinoleoyl cardiolipin (L4CL, m/z 723.8→m/z 279.4) in heart tissue from TAZ knockdown mice treated with either vehicle control or TAZ-Antp.
Figure 12B:
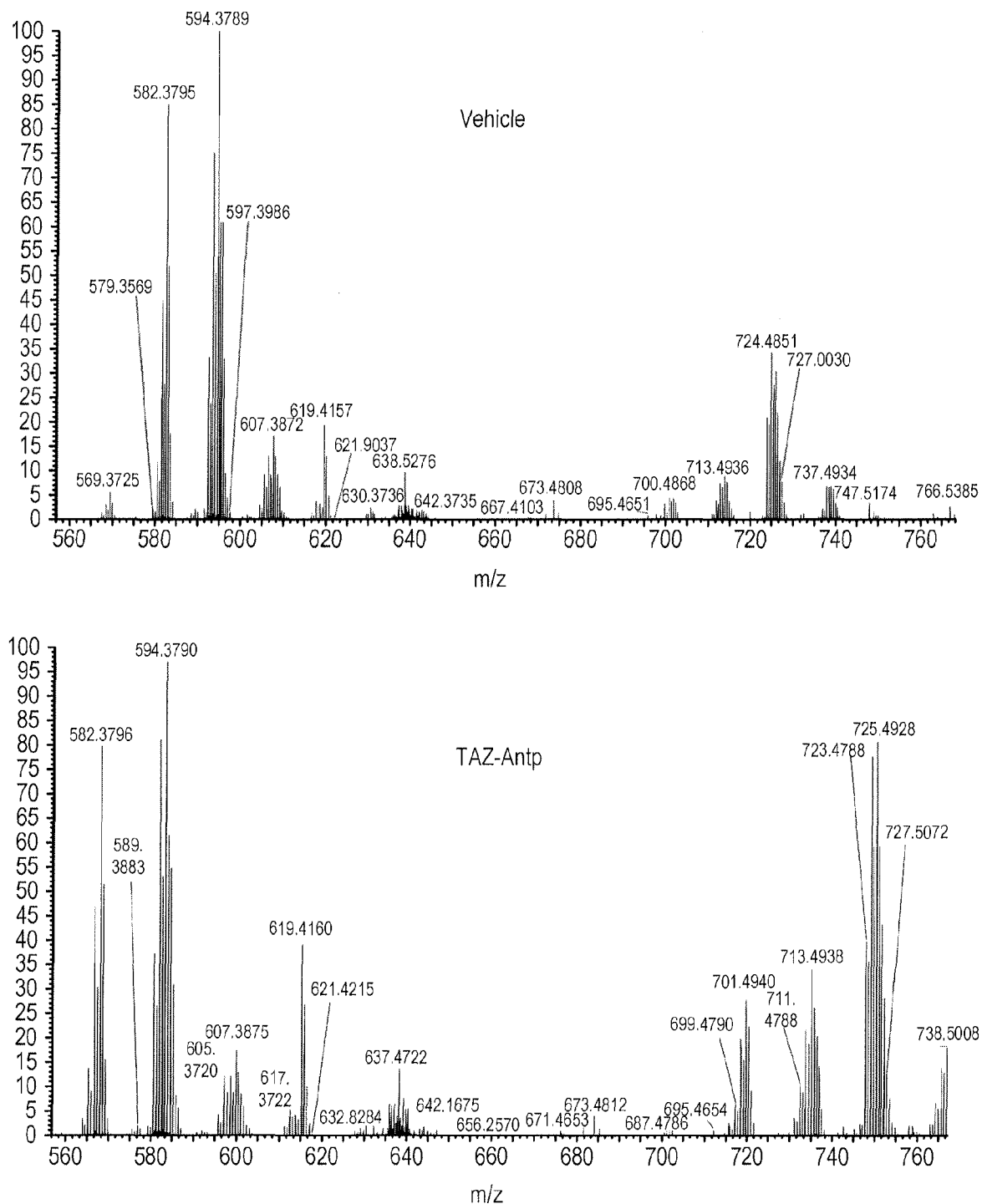
FIG. 12B are LC-MS spectra of cardiolipin from TAZ knockdown mice hearts treated with either vehicle control or TAZ-Antp.
Figure 12C:
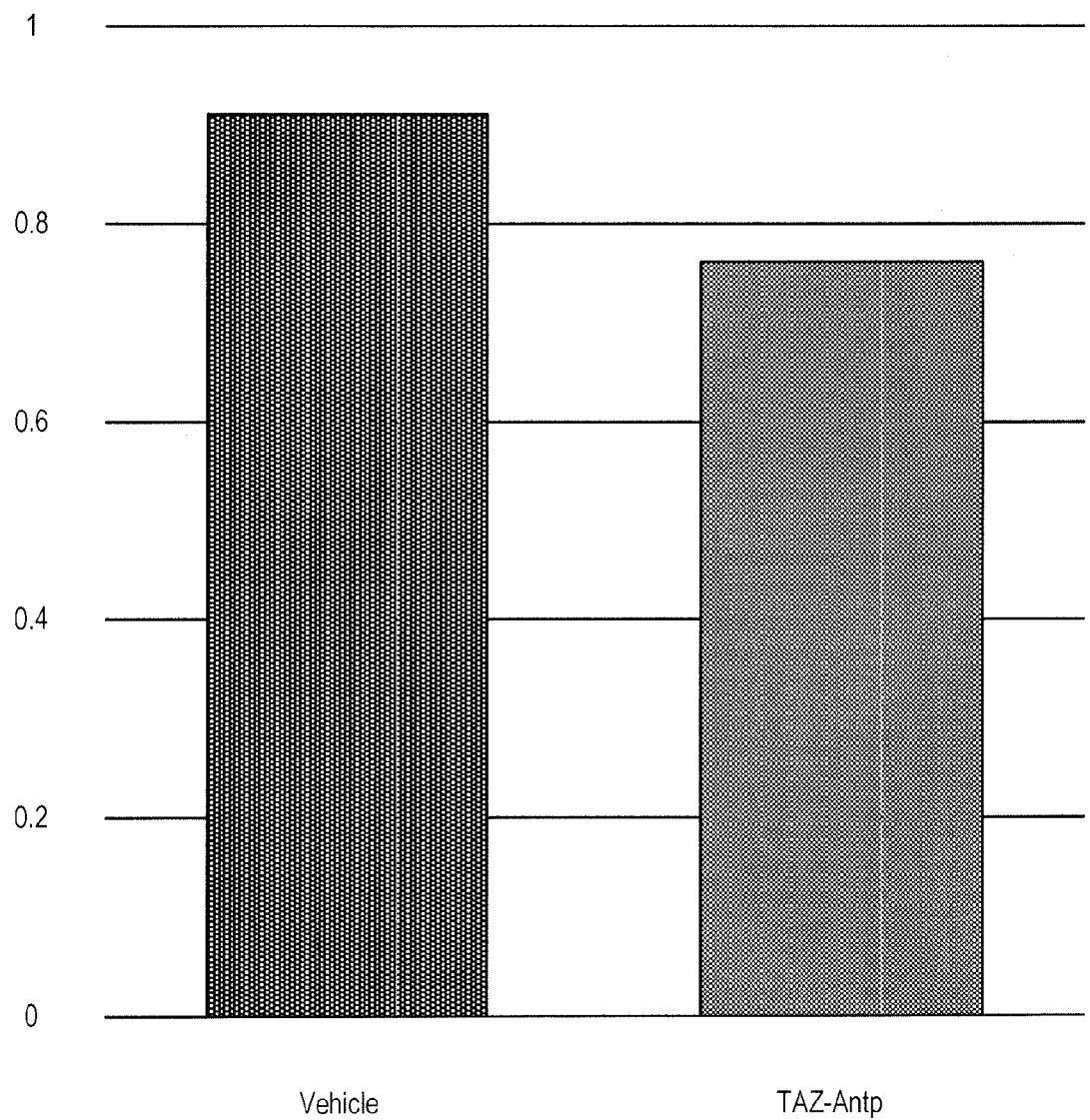
FIG. 12C is a graph depicting the MLCL/L4CL ratio in hearts from TAZ-Antp and vehicle control treated TAZ knockdown mice.
Figure 12D:
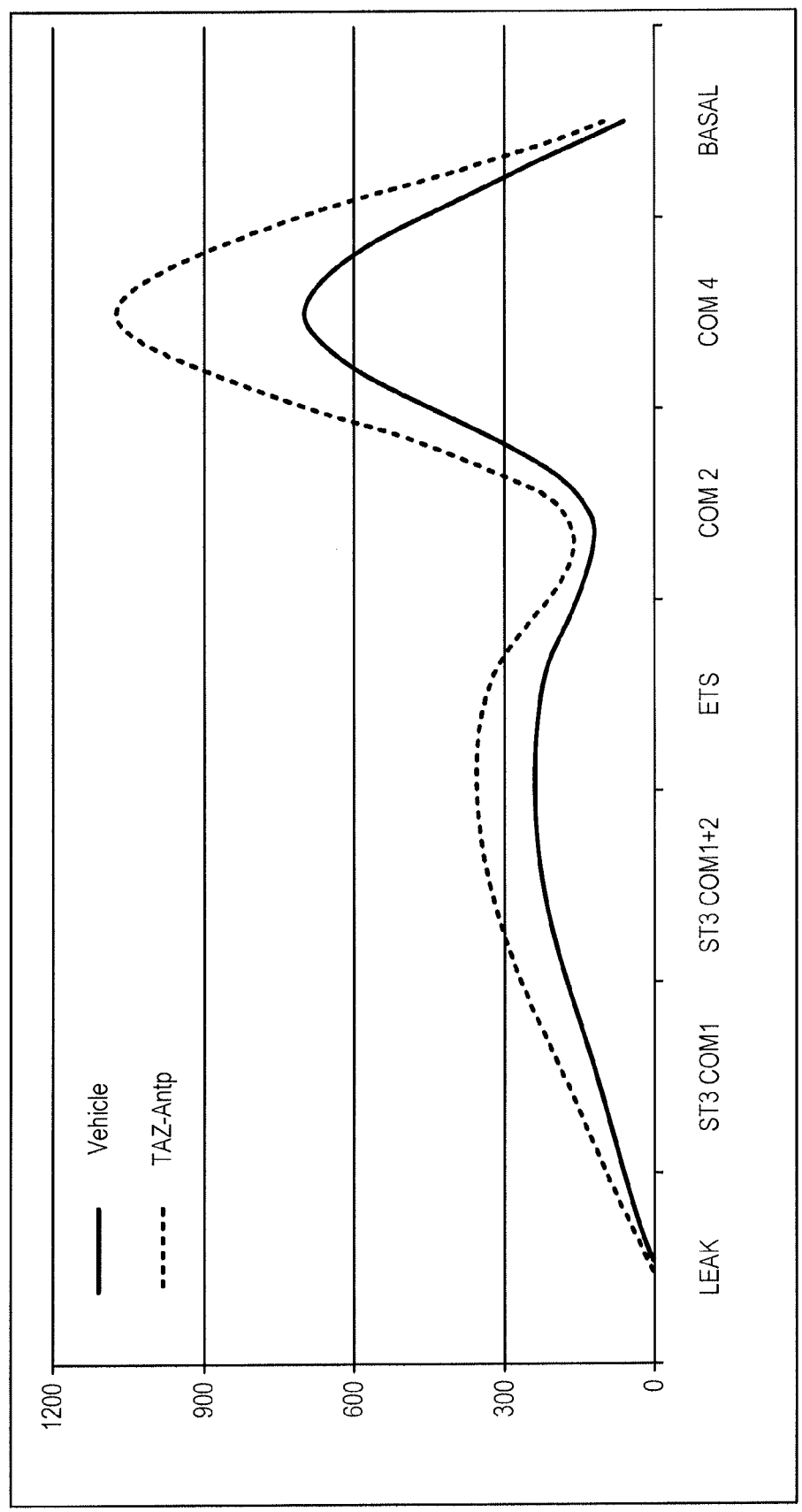
FIG. 12D is a graph depicting oxygen consumption rates in TAZ knockdown mice hearts measured with a high resolution Oxygraph2k respirometer after treatment with either TAZ-Antp or vehicle control.

As a step in optimizing protein delivery to the heart, TAZ-CTP was also delivered via coronary artery perfusion, with about 5% of cells demonstrating uptake by immunofluorescence (see FIG. 11). These findings may demonstrate that delivery of tafazzin to the heart to can rescue defective mitochondrial respiration.

Example 20

Systemic Infusion of Recombinant Tafazzin Alters the MLCL:L4CL Ratio and Augments Mitochondrial Respiration in Tafazzin-Deficient Hearts To determine whether recombinant tafazzin can be administered systemically, alter the MLCL:L4CL ratio, and improve mitochondrial respiration in the tafazzin-deficient heart, TAZ-KD mice were injected with either 40 µg recombinant TAZ-Antp or vehicle control retroorbitally every other day and then the hearts were harvested on day 8 for LC-MS or oxygraph measurements. Mitochondrial respiration was measured in an Oroboros™ Oxygraph Chamber as previously described (Dai D F, et al. (2011) Circ. Res. 108, 837-846 and N'Guessan B, et al, (2004) Mol. Cell Biochem. 256-257, 267-80). Equal amounts of heart samples were homogenized immediately prior to respirometric measurements, then added to measurement chambers. Leak respiration was measured prior to addition of any substrates. State 3, Complex I activity was measured after the addition of malate, pyruvate, and glutamate; state 3, Complex I and II activity was measured after the addition of ADP and cytochrome C; the electron transport system (ETS) was measured after the addition of CCCP; Complex II activity was measured after the addition of antimycin A; non-mitochondrial respiration was measured after the addition of rotenone and this value was subtracted from all other measurements; Complex IV activity after the addition of ascorbate and tetramethyl phenylenediamine (TMPD) and basal respiration was measured after the addition of potassium cyanide and this value was subtracted from the Complex IV value. As shown in FIGS. 12A-12D, recombinant TAZ-Antp administered systemically can shift the MLCL:L4CL ratio and increase activity of all, or substantially all, measured mitochondrial complexes in TAZ-KD heart tissue.

Example 21

Determine Whether TAZ-Deficient Neonatal Myocytes Demonstrate Increased ROS Generation, Increased Susceptibility to Hypertrophy and Increased Apoptosis Without being bound by theory, it is hypothesized that TAZ deficiency may lead to increased ROS generation and greater hypertrophy than WT controls. Neonatal cardiomyocytes from TAZ-knockdown mice can be cultured and their susceptibility to hypertrophy induced by phenylephrine, angiotensin II, and serum can be compared. The induction of ROS by hypertrophic stimuli can also be assessed. Additionally, apoptosis in response to oxidative and ER stress can be assessed. TAZ-deficient myocytes may demonstrate increased ROS, hypertrophy, and apoptosis.

Example 22

Isolation of Neonatal Mouse Cardiac Myocytes

Both adult and neonatal mouse cardiac myocytes have been successfully cultured, as shown above and described previously (see Xiang F, et al. (2006) Am. J. Physiol.-Heart C. 290, H1997-H2006). Neonatal cardiac myocytes can be harvested by a modification of the method of Springhorn and Claycomb (see (1989) Biochem. J. 258, 73-78). Hearts can be removed, trimmed of atria and vascular tissue, and the remaining ventricular tissue from each heart can be cut into several pieces. Tissue can be incubated in trypsin/EDTA (Cambrex™ CC-5012, 0.25 mg/ml, 5 mL for 8-10 ventricles) with rotation at 4° C. for 30 minutes. Cells can be collected by centrifugation at 1800 rpm for 5 minutes, followed by removal of supernatant and resuspension in DMEM (Gibco®, Cat. No. 11995-065, with Penicillin, Streptomycin, and Fungizone) supplemented with 20% FCS. Subsequently, cells can be collected by centrifugation, resuspended in 4 mL of collagenase type II solution (1 mg/ml) in HBSS, transferred to a p60 dish, and placed at 37° C. Cells can then be pipetted every 10 minutes until dispersed (up to 30-40 minutes), and filtered with a 70 µm nylon cell strainer (FALCON™ 35-2350) on a 50 mL tube to remove tissue debris. Collagenase can be neutralized in the filtrate by the addition of DMEM, 20% FCS. Cells can be collected by centrifugation at 800 rpm for 5 minutes, resuspended in 10 ml of DMEM, 20% FCS, and incubated on a p100 dish at 37° C. for 1-2 hour(s) to remove fibroblasts. The nonadherent cells can be collected by centrifugation of the culture medium at 800 rpm for 5 minutes, resuspended in 10.5 ml of DMEM, 20% FCS, and the number of cells can be quantified by Coulter counting. Cells are seeded onto fibronectin-coated dishes at a density of $1 \times 10^5$/well in a 24-well plate for hypertrophy assays and $3-5 \times 10^6$ cells onto a p60 dish for other purposes. 20 µM Ara-C can be included in the culture medium to inhibit proliferation of any contaminating fibroblasts.

Example 23

Induction and Assessment of Hypertrophy in Cultured Neonatal Mouse Cardiac Myocytes Neonatal cardiac myocytes can be isolated as described above. For hypertrophy assays, cells can be stimulated with media containing 20% serum or media without serum supplemented with 30 µM phenylephrine (with 2 µM timolol), 100 nM angiotensin II, or 1 µM isoproterenol. Protein can be harvested at 0 minutes, 1 minute, 3 minutes, 15 minutes, and 60 minutes after stimulation for analysis of signaling responses by Western blotting. Some cells can be cultured up to 48 hours after stimulation to verify that hypertrophy has been induced. These cells can be assessed for hypertrophy in 2 different assays. Cells can be immunostained for sarcomeric myosin heavy chain with MF-20 monoclonal antibody (Developmental Studies Hybridoma Bank) and cell size can be quantified by digital image capture and quantitative morphometry, as has been done previously (see Xiang F, et al. (2006) Am. J. Physiol.-Heart C. 290, H1997-H2006). In addition, treated cells can be cultured in the presence of $^3$H-leucine to measure protein synthesis. After 24 hours of stimulation, cells can be pulse-labeled with 1.0 µCi/ml [$^3$H]leucine for an additional 6 hours. The medium can be aspirated and the cells can be washed with ice-cold PBS and fixed on ice for 30 minutes with cold 10% TCA. After washing twice with 5% TCA, and once with water, the radioactivity incorporated into the TCA-precipitable material can be determined by liquid scintillation counting after solubilization in 0.25 M NaOH.

Example 24

Assessment of ROS Induction and Hypertrophic Signaling

To detect mitochondrial ROS, cultured neonatal myocytes can be stained with MitoSOX Red and MitoTracker Green at baseline and after 48 hours of hypertrophic stimulation, according to the manufacturer's instructions, as discussed above. Cell lysates can also be analyzed by Western blotting for phosphorylated and/or non-phosphorylated forms of kinases associated with different hypertrophic signaling pathways including, but not limited to, MAPKs, (ERK1/2, JNK, p38), CaMKII, p70S6, AKT, gp130, erbB2, Ras, Rac1, and GSK-3β.

Example 25

Assessment of the Apoptotic Response to Oxidative and Endoplasmic Reticulum Stress in Cultured Neonatal Mouse Cardiomyocytes Cardiomyocytes can be prepared and cultured, as above, for the assessment of their apoptotic response to oxidative and endoplasmic reticulum (ER) stress as has been done previously (see Liu Y, et al. (2010) Am. J. Physiol.-Heart C. 298, H2082-H2092 and Yu M, et al. (2009) OMICS, 13, 501-511). The cultured neonatal cardiomyocyte apoptotic response to oxidative stress can be tested by treating with $H_2O_2$ (100 μM) for 24 hours, apoptotic response to ER stress can also be tested by treating with tunicamycin (100 ng/ml) for 48 hours. After treatment, apoptotic cells can be detected using TUNEL staining to detect DNA fragmentation using a commercially available kit (Roche Molecular Diagnostics™). Alternatively, cells can undergo annexin V staining followed by flow cytometry. In brief, myocytes can be stained with annexin V by using the Annexin-V-FLUOS staining kit (Becton Dickinson™) according to the manufacturer's instructions. To exclude necrotic cells from the analysis, cells can also be incubated with propidium iodide. Cells can be analyzed (10,000 cells per sample) using a FACScan flow cytometer (Becton Dickinson™) with CELL-QUEST™ flow cytometric analysis software. Propidium iodide-positive cells are necrotic and can be excluded from analysis.

Neonatal myocytes from TAZ-KD mice may demonstrate increased hypertrophy and increased ROS production after hypertrophic stimulation when compared to WT control cells. Increased ROS may be associated with increased signaling through the ERK and AKT pathways. TAZ-KD cardiomyocytes may be more susceptible to apoptosis induced by oxidative and ER stress. In some embodiments, increased susceptibility to hypertrophy, increase in ROS, or increased apoptosis in the TAZ-KD myocytes may not be observed. In some such embodiments, the mechanism of cardiomyopathy in tafazzin deficiency may not involve ROS and may involve other mechanisms such as effects on cardiac fibroblasts.

Example 26

Determine Whether ROS Generation and Susceptibility to Cardiac Hypertrophy and Heart Failure are Increased in TAZ-Knockdown Mice Without being bound by theory, it is hypothesized that TAZ-KD mice may demonstrate greater ROS generation and increased susceptibility to hypertrophy and heart failure after pressure overload or AngII infusion. TAZ-KD mice may undergo baseline echocardiography and then transverse aortic constriction surgery or AngII infusion, followed by organ harvest for gravimetry and histology. TAZ-KD mice may develop excessive hypertrophy, worse heart failure, and increased ROS generation.

Example 27

Induction of Hypertrophy by Transverse Aortic Constriction or AngII Infusion and Analysis of Heart Tissue Tafazzin-deficient mice can reportedly develop diastolic dysfunction early (see Phoon C K L, et al. (2012) J Am. Heart Assoc. 1, jah3-e000455-jah000453-e000455) and systolic dysfunction relatively late (Acehan D, et al. J. Biol. Chem. 286, 899-908). Late onset of cardiomyopathy in this model may suggest that other stressors may be involved, such as hypertension. TAZ-KD and WT mice can be raised to the age of 8 weeks to 12 weeks and can be divided into 4 groups of 10 as follows: 1) WT, sham operation; 2) TAZ-KD, sham operation; 3) WT, aortic banding; and 4) TAZ-KD, aortic banding. Animals can undergo echocardiography followed by either aortic banding or sham operation as described previously (see Liu Y, et al. (2010) Am. J. Physiol.-Heart C. 298. H2082-H2092; Yu M, et al. (2009) OMICS 13, 501-511; and Liao R, et al. (20020 Circulation 106, 2125-2131). Briefly, mice can be anesthetized with avertin, then ventilated. The ascending aorta can be exposed by anterolateral thoracotomy and then constricted by tying a 7-0 silk suture around the aorta and a 27 gauge needle. Sham operated mice can undergo thoracotomy but not aortic constriction. Mice can undergo serial echocardiography at 1 week, 2 weeks, 3 weeks, and 4 weeks followed by euthanasia, harvesting of hearts, measurement of ventricular weight to body weight ratio, and measurement of ventricular weight to tibia length ratio followed by histology. Hypertrophy can also be induced by angiotensin II osmotic minipump infusion as previously described (see Xiang F, et al. (2006) Am. J. Physiol.-Heart C. 290, H1997-H2006), in four groups analogous to those described for TAC, with similar echocardiographic and gravimetric analysis.

Explanted hearts from treated animals can undergo routine histological analysis using standard stains such as hematoxylin/eosin and Masson trichrome to observe for inflammation and fibrosis. Apoptosis can also be assessed using TUNEL staining. Oxidative stress can be assessed by immunostaining for 3-nitrotyrosine (3-NT), a marker of oxidative and nitrosative stress. $F_2$-isoprostane levels can be measured within homogenized heart tissue, using LC-MS. $F_2$-isoprostane detection can be a marker of lipid peroxidation.

TAZ-KD mice may develop more hypertrophy and worse heart failure after TAC or AngII compared to WT controls. Furthermore, increased fibrosis, apoptosis, 3-NT staining, and F2 isoprostane levels may be observed. In some embodiments, significant differences in hypertrophy, heart failure, or oxidative stress may not be observed in TAZ-KD mice. In some such embodiments, the above-described analysis could be modified using isoproterenol or phenylephrine infusion via osmotic minipump, as has been done previously (see Xiang F, et al. (2006) Am. J. Physiol.-Heart C. 290, H1997-H2006).

Example 28

Determine Whether Exogenous TAZ can Suppress Pathological Hypertrophy and Heart Failure In Vitro and In Vivo in Both TAZ-Deficient and WT Cells A soluble tafazzin protein engineered for uptake into cells has been developed and it has been shown that the soluble tafazzin protein can augment defective mitochondrial respiration in both cultured cells and tafazzin-deficient hearts. Without being bound by theory, it is hypothesized that exogenous tafazzin may suppress ROS generation and ameliorate hypertrophy in both TAZ-deficient and WT cells. TAZ-KD and WT neonatal myocytes treated with hypertrophic stimuli can be concurrently treated with soluble tafazzin with or without a CPP peptide. Similarly, TAZ-KD and WT mice undergoing aortic banding can be treated with soluble tafazzin with or without a CPP peptide, administered systemically. TAZ with CPPs may suppress ROS generation, blunt the hypertrophic response, suppress apoptosis, and ameliorate heart failure.

Example 29

Effects of Recombinant TAZ on Hypertrophy and Apoptosis In Vitro

Neonatal myocytes can be cultured from WT and TAZ-KD mice, as described above, and tested for hypertrophy, ROS generation, signal transduction, and apoptosis, as described above. To assess the effectiveness of recombinant TAZ, cells induced with hypertrophic or apoptotic stimuli can be treated concurrently with recombinant TAZ with or without a cell penetrating peptide at 10 µg/ml for 48 hours. Cell size, 3H-leucine uptake, induction of ROS, activation of signaling pathways, and induction of apoptosis, as described above, can be tested.

Example 30

Effects of Recombinant TAZ on Hypertrophy and Heart Failure In Vivo

TAC or AngII infusion can be performed on WT and TAZ-KD mice as described above but it can also be determined whether exogenous recombinant TAZ can rescue ROS generation and progression to hypertrophy and heart failure. Recombinant tafazzin can be administered systemically by retroorbital injection at weekly intervals or by prolonged infusion by osmotic minipump over 4 weeks. The effects of tafazzin on systolic and diastolic function can be assessed using echocardiography. Uptake into myocardium, effects on cardiolipin metabolism, mitochondrial respiration, oxidative stress, inflammation, fibrosis, and apoptosis can be assessed as described above.

Administration of recombinant TAZ to neonatal myocyte cultures may blunt the hypertrophic response, limit ROS generation, and decrease apoptosis in TAZ-KD cells. Recombinant TAZ may also improve these parameters in WT cells. The systemic administration of tafazzin to tafazzin-deficient mice concurrently with TAC may lead to uptake into heart muscle, improved cardiolipin modification, improved mitochondrial respiration, reduced hypertrophy, heart failure, apoptosis, and fibrosis in TAZ-KD mice. Local and systemic administration of tafazzin may also improve diastolic and systolic dysfunction in tafazzin-deficient hearts. Exogenous tafazzin may improve these parameters in wild-type mice as well.

In some embodiments, recombinant TAZ may not affect hypertrophy, ROS generation, or apoptosis in vitro. In some embodiments, pretreatment prior to hypertrophic stimulation rather than concurrent treatment may be conducted. For in vivo studies, tafazzin-deficient muscles may not take up tafazzin protein as efficiently as compared to cells after systemic administration. In various embodiments, systemic administration may not lead to cardiolipin modification, enhanced mitochondrial respiration, or enhanced cardiac muscle function as measured by echocardiography. In some such embodiments, the dose or duration of therapy may be increased using an alternate route such as intravenous or intraarterial injection into coronary arteries.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

It will be apparent to those having skill in the art that many changes may be made to the details of the above-described embodiments without departing from the underlying principles of the invention. The scope of the present invention should, therefore, be determined only by the following claims.

The invention claimed is:

1. An isolated and purified fusion protein comprising:
a tafazzin peptide; and
a cellular permeability peptide.

2. The isolated and purified fusion protein of claim 1, wherein the tafazzin peptide is coupled to the cellular permeability peptide through a polypeptide linker.

3. The isolated and purified fusion protein of claim 2, comprising a peptide selected from the group consisting of SEQ ID NO: 10, SEQ ID NO: 11, SEQ ID NO: 12, and SEQ ID NO: 13.

4. The isolated and purified fusion protein of claim 1, wherein the tafazzin peptide is selected from the group consisting of SEQ ID NO: 1, SEQ ID NO: 2, SEQ ID NO: 3, SEQ ID NO: 4, and SEQ ID NO: 5.

5. The isolated and purified fusion protein of claim 1, wherein the cellular permeability peptide is an antennapedia permeability peptide.

6. The isolated and purified fusion protein of claim 5, wherein the antennapedia permeability peptide comprises SEQ ID NO: 6.

7. The isolated and purified fusion protein of claim 1, wherein the cellular permeability peptide is an HIV Tat permeability peptide.

8. The isolated and purified fusion protein of claim 7, wherein the HIV Tat permeability peptide comprises SEQ ID NO: 7.

9. The isolated and purified fusion protein of claim 1, wherein the cellular permeability peptide is a cardiac targeting peptide (CTP).

10. The isolated and purified fusion protein of claim 9, wherein the CTP comprises SEQ ID NO: 8.

11. The isolated and purified fusion protein of claim 1, wherein the cellular permeability peptide is a Kaposi FGF4-permeability peptide.

12. The isolated and purified fusion protein of claim 11, wherein the Kaposi FGF4-permeability peptide comprises SEQ ID NO: 9.

13. A method for treating a patient having a disorder associated with a tafazzin deficiency or a remodeled cardiolipin deficiency, comprising:
administering to the patient an effective amount of a pharmaceutical composition comprising:
a fusion protein comprising a tafazzin peptide and a cellular permeability peptide; and
a pharmaceutically acceptable carrier
to reduce a pathological effect or symptom of the disorder associated with the tafazzin deficiency or the remodeled cardiolipin deficiency.

14. The method of claim 13, wherein the tafazzin deficiency or the remodeled cardiolipin deficiency is associated with a tafazzin gene (TAZ) mutation.

15. The method of claim 13, wherein the disorder associated with a tafazzin deficiency or the remodeled cardiolipin deficiency is Barth syndrome.

16. The method of claim 13, wherein the tafazzin peptide is selected from the group consisting of SEQ ID NO: 1, SEQ ID NO: 2, SEQ ID NO: 3, SEQ ID NO: 4, and SEQ ID NO: 5.

17. The method of claim 3, wherein the cellular permeability peptide is selected from at least one of an antennapedia permeability peptide, an HIV Tat permeability peptide, a cardiac targeting peptide (CTP), or a Kaposi FGF4-permeability peptide.

18. A method of treating a patient having or at risk of developing, Barth syndrome, comprising:
administering to the patient an effective amount of a pharmaceutical composition comprising:
a fusion protein comprising a tafazzin peptide and a permeability peptide; and
a pharmaceutically acceptable carrier
to reduce a pathological effect or symptom of Barth syndrome, or to reduce the risk of developing Barth syndrome.

19. The method of claim 18, wherein the fusion protein is selected from the group consisting of SEQ ID NO: 10, SEQ ID NO: 11, SEQ ID NO: 12, and SEQ ID NO: 13.

20. The method of claim 13, wherein the cellular permeability peptide comprises a peptide selected from the group consisting of SEQ ID NO: 6, SEQ ID NO: 7, SEQ ID NO: 8, and SEQ ID NO: 9.

21. The method of claim 13, wherein the fusion protein comprises a peptide selected from the group consisting of SEQ ID NO: 10, SEQ ID NO: 11, SEQ ID NO: 12, and SEQ ID NO: 13.

22. The method of claim 18, wherein the tafazzin peptide is selected from the group consisting of SEQ ID NO: 1, SEQ ID NO: 2, SEQ ID NO: 3, SEQ ID NO: 4, and SEQ ID NO: 5.

23. The method of claim 18, wherein the cellular permeability peptide is an antennapedia permeability peptide.

24. The method of claim 23, wherein the antennapedia permeability peptide comprises SEQ ID NO: 6.

25. The method of claim 18, wherein the cellular permeability peptide is an HIV Tat permeability peptide.

26. The method of claim 25, wherein the HIV Tat permeability peptide comprises SEQ ID NO: 7.

27. The method of claim 18, wherein the cellular permeability peptide is a cardiac targeting peptide (CTP).

28. The method of claim 27, wherein the CTP comprises SEQ ID NO: 8.

29. The method of claim 18, wherein the cellular permeability peptide is a Kaposi FGF4-permeability peptide.

30. The method of claim 29, wherein the Kaposi FGF4-permeability peptide comprises SEQ ID NO: 9.

\* \* \* \* \*

SEQUENCE LISTING

```
<160> NUMBER OF SEQ ID NOS: 17

<210> SEQ ID NO 1
<211> LENGTH: 292
<212> TYPE: PRT
<213> ORGANISM: Homo sapiens

<400> SEQUENCE: 1

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Ala Glu Phe Phe
        115                 120                 125
```

```
Gln Ala Glu Asn Glu Gly Lys Gly Val Leu Asp Thr Gly Arg His Met
        130                 135                 140

Pro Gly Ala Gly Lys Arg Glu Lys Gly Asp Gly Val Tyr Gln Lys
145                 150                 155                 160

Gly Met Asp Phe Ile Leu Glu Lys Leu Asn His Gly Asp Trp Val His
                165                 170                 175

Ile Phe Pro Glu Gly Lys Val Asn Met Ser Ser Glu Phe Leu Arg Phe
                180                 185                 190

Lys Trp Gly Ile Gly Arg Leu Ile Ala Glu Cys His Leu Asn Pro Ile
                195                 200                 205

Ile Leu Pro Leu Trp His Val Gly Met Asn Asp Val Leu Pro Asn Ser
        210                 215                 220

Pro Pro Tyr Phe Pro Arg Phe Gly Gln Lys Ile Thr Val Leu Ile Gly
225                 230                 235                 240

Lys Pro Phe Ser Ala Leu Pro Val Leu Glu Arg Leu Arg Ala Glu Asn
                245                 250                 255

Lys Ser Ala Val Glu Met Arg Lys Ala Leu Thr Asp Phe Ile Gln Glu
                260                 265                 270

Glu Phe Gln His Leu Lys Thr Gln Ala Glu Gln Leu His His Asn His Leu
        275                 280                 285

Gln Pro Gly Arg
        290

<210> SEQ ID NO 2
<211> LENGTH: 262
<212> TYPE: PRT
<213> ORGANISM: Homo sapiens

<400> SEQUENCE: 2

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
                20                  25                  30

Cys Phe Trp Thr Lys Tyr Met Asn His Leu Thr Val His Asn Arg Glu
            35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
```

```
            195                 200                 205
Ile Gly Lys Pro Phe Ser Ala Leu Pro Val Leu Glu Arg Leu Arg Ala
            210                 215                 220
Glu Asn Lys Ser Ala Val Glu Met Arg Lys Ala Leu Thr Asp Phe Ile
225                 230                 235                 240
Gln Glu Glu Phe Gln His Leu Lys Thr Gln Ala Glu Gln Leu His Asn
                245                 250                 255
His Leu Gln Pro Gly Arg
            260

<210> SEQ ID NO 3
<211> LENGTH: 262
<212> TYPE: PRT
<213> ORGANISM: Mus musculus

<400> SEQUENCE: 3

Met Pro Leu His Val Lys Trp Pro Phe Pro Ala Val Pro Arg Leu Thr
1               5                   10                  15
Trp Thr Leu Ala Ser Ser Val Val Met Gly Leu Val Gly Thr Tyr Ser
            20                  25                  30
Cys Phe Trp Thr Lys Tyr Met Asn His Leu Thr Val His Asn Lys Glu
        35                  40                  45
Val Leu Tyr Glu Leu Ile Glu Asn Arg Gly Pro Ala Thr Pro Leu Ile
    50                  55                  60
Thr Val Ser Asn His Gln Ser Cys Met Asp Asp Pro His Leu Trp Gly
65                  70                  75                  80
Ile Leu Lys Leu Arg His Ile Trp Asn Leu Lys Leu Met Arg Trp Thr
                85                  90                  95
Pro Ala Ala Ala Asp Ile Cys Phe Thr Lys Glu Leu His Ser His Phe
            100                 105                 110
Phe Ser Leu Gly Lys Cys Val Pro Val Cys Arg Gly Asp Gly Val Tyr
        115                 120                 125
Gln Lys Gly Met Asp Phe Ile Leu Glu Lys Leu Asn His Gly Asp Trp
    130                 135                 140
Val His Ile Phe Pro Glu Gly Lys Val Asn Met Ser Ser Glu Phe Leu
145                 150                 155                 160
Arg Phe Lys Trp Gly Ile Gly Arg Leu Ile Ala Glu Cys His Leu Asn
                165                 170                 175
Pro Ile Ile Leu Pro Leu Trp His Val Gly Met Asn Asp Val Leu Pro
            180                 185                 190
Asn Ser Pro Pro Tyr Phe Pro Arg Phe Gly Gln Lys Ile Thr Val Leu
        195                 200                 205
Ile Gly Lys Pro Phe Ser Thr Leu Pro Val Leu Glu Arg Leu Arg Ala
    210                 215                 220
Glu Asn Lys Ser Ala Val Glu Met Arg Lys Ala Leu Thr Asp Phe Ile
225                 230                 235                 240
Gln Glu Glu Phe Gln Arg Leu Lys Met Gln Ala Glu Gln Leu His Asn
                245                 250                 255
His Phe Gln Pro Gly Arg
            260

<210> SEQ ID NO 4
<211> LENGTH: 262
<212> TYPE: PRT
<213> ORGANISM: Artificial Sequence
<220> FEATURE:
```

<223> OTHER INFORMATION: Human-mouse chimeric protein

<400> SEQUENCE: 4

```
Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Thr Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
                245                 250                 255

His Phe Gln Pro Gly Arg
            260
```

<210> SEQ ID NO 5
<211> LENGTH: 262
<212> TYPE: PRT
<213> ORGANISM: Artificial Sequence
<220> FEATURE:
<223> OTHER INFORMATION: Mouse-human chimeric protein

<400> SEQUENCE: 5

```
Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80
```

```
Ile Leu Lys Leu Arg His Ile Trp Asn Leu Lys Leu Met Arg Trp Thr
            85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
            115                 120                 125

Gln Lys Gly Met Asp Phe Ile Leu Glu Lys Leu Asn His Gly Asp Trp
            130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
            165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
            195                 200                 205

Ile Gly Lys Pro Phe Ser Thr Leu Pro Val Leu Glu Arg Leu Arg Ala
            210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
            245                 250                 255

His Phe Gln Pro Gly Arg
            260

<210> SEQ ID NO 6
<211> LENGTH: 16
<212> TYPE: PRT
<213> ORGANISM: Artificial Sequence
<220> FEATURE:
<223> OTHER INFORMATION: Antennapedia permeability peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: HIV Tat permeability peptide

<400> SEQUENCE: 7

Tyr Gly Arg Lys Lys Arg Arg Gln Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Cardiac Targeting Peptide (CTP)

<400> SEQUENCE: 8

Ala Pro Trp His Leu Ser Ser Gln Tyr Ser Arg Thr
1               5                   10

<210> SEQ ID NO 9
<211> LENGTH: 12
```

```
-continued

<212> TYPE: PRT
<213> ORGANISM: Artificial Sequence
<220> FEATURE:
<223> OTHER INFORMATION: Kaposi FGF4-derived peptide

<400> SEQUENCE: 9

Ala Ala Val Leu Leu Pro Val Leu Leu Ala Ala Pro
1               5                   10

<210> SEQ ID NO 10
<211> LENGTH: 291
<212> TYPE: PRT
<213> ORGANISM: Artificial Sequence
<220> FEATURE:
<223> OTHER INFORMATION: Mouse TAZ-Antp

<400> SEQUENCE: 10

Met Pro Leu His Val Lys Trp Pro Phe Pro Ala Val Pro Arg Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Lys Glu
        35                  40                  45

Val Leu Tyr Glu Leu Ile Glu Asn Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Thr Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
                245                 250                 255

His Phe Gln Pro Gly Arg Leu Glu Glu Ser Gly Gly Gly Ser Arg
            260                 265                 270

Gln Ile Lys Ile Trp Phe Gln Asn Arg Arg Met Lys Trp Lys Lys Gly
    275                 280                 285

Ser Gly Cys
    290

<210> SEQ ID NO 11
```

<211> LENGTH: 291
<212> TYPE: PRT
<213> ORGANISM: Artificial Sequence
<220> FEATURE:
<223> OTHER INFORMATION: Human TAZ-Antp

<400> SEQUENCE: 11

```
Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Ala Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln His Leu Lys Thr Gln Ala Glu Gln Leu His Asn
                245                 250                 255

His Leu Gln Pro Gly Arg Val Glu Glu Ser Gly Gly Gly Ser Arg
            260                 265                 270

Gln Ile Lys Ile Trp Phe Gln Asn Arg Arg Met Lys Trp Lys Lys Gly
        275                 280                 285

Ser Gly Cys
    290
```

<210> SEQ ID NO 12
<211> LENGTH: 288
<212> TYPE: PRT
<213> ORGANISM: Artificial Sequence
<220> FEATURE:
<223> OTHER INFORMATION: Mouse TAZ-CTP

<400> SEQUENCE: 12

```
Met Pro Leu His Val Lys Trp Pro Phe Pro Ala Val Pro Arg Leu Thr
1               5                   10                  15

Trp Thr Leu Ala Ser Ser Val Val Met Gly Leu Val Gly Thr Tyr Ser
```

-continued

```
                20                  25                  30
    Cys Phe Trp Thr Lys Tyr Met Asn His Leu Thr Val His Asn Lys Glu
                    35                  40                  45

Val Leu Tyr Glu Leu Ile Glu Asn Arg Gly Pro Ala Thr Pro Leu Ile
     50                  55                  60

Thr Val Ser Asn His Gln Ser Cys Met Asp Asp Pro His Leu Trp Gly
     65                  70                  75                  80

Ile Leu Lys Leu Arg His Ile Trp Asn Leu Lys Leu Met Arg Trp Thr
                     85                  90                  95

Pro Ala Ala Asp Ile Cys Phe Thr Lys Glu Leu His Ser His Phe
                    100                 105                 110

Phe Ser Leu Gly Lys Cys Val Pro Val Cys Arg Gly Asp Gly Val Tyr
                    115                 120                 125

Gln Lys Gly Met Asp Phe Ile Leu Glu Lys Leu Asn His Gly Asp Trp
                    130                 135                 140

Val His Ile Phe Pro Glu Gly Lys Val Asn Met Ser Ser Glu Phe Leu
    145                 150                 155                 160

Arg Phe Lys Trp Gly Ile Gly Arg Leu Ile Ala Glu Cys His Leu Asn
                    165                 170                 175

Pro Ile Ile Leu Pro Leu Trp His Val Gly Met Asn Asp Val Leu Pro
                    180                 185                 190

Asn Ser Pro Pro Tyr Phe Pro Arg Phe Gly Gln Lys Ile Thr Val Leu
                    195                 200                 205

Ile Gly Lys Pro Phe Ser Thr Leu Pro Val Leu Glu Arg Leu Arg Ala
                    210                 215                 220

Glu Asn Lys Ser Ala Val Glu Met Arg Lys Ala Leu Thr Asp Phe Ile
    225                 230                 235                 240

Gln Glu Glu Phe Gln Arg Leu Lys Met Gln Ala Glu Gln Leu His Asn
                    245                 250                 255

His Phe Gln Pro Gly Arg Leu Glu Ser Gly Gly Gly Ser Pro Gly
                    260                 265                 270

Ala Pro Trp His Leu Ser Ser Gln Tyr Ser Arg Thr Gly Ser Gly Cys
                    275                 280                 285
```

<210> SEQ ID NO 13
<211> LENGTH: 318
<212> TYPE: PRT
<213> ORGANISM: Artificial Sequence
<220> FEATURE:
<223> OTHER INFORMATION: Human TAZ-CTP

<400> SEQUENCE: 13

```
Met Pro Leu His Val Lys Trp Pro Phe Pro Ala Val Pro Pro Leu Thr
 1               5                  10                  15

Trp Thr Leu Ala Ser Ser Val Val Met Gly Leu Val Gly Thr Tyr Ser
                20                  25                  30

Cys Phe Trp Thr Lys Tyr Met Asn His Leu Thr Val His Asn Arg Glu
                35                  40                  45

Val Leu Tyr Glu Leu Ile Glu Lys Arg Gly Pro Ala Thr Pro Leu Ile
 50                  55                  60

Thr Val Ser Asn His Gln Ser Cys Met Asp Asp Pro His Leu Trp Gly
 65                  70                  75                  80

Ile Leu Lys Leu Arg His Ile Trp Asn Leu Lys Leu Met Arg Trp Thr
                 85                  90                  95

Pro Ala Ala Ala Asp Ile Cys Phe Thr Lys Glu Leu His Ser His Phe
```

```
                100             105              110
    Phe Ser Leu Gly Lys Cys Val Pro Val Cys Arg Gly Ala Glu Phe Phe
                115                 120                 125
    Gln Ala Glu Asn Glu Gly Lys Gly Val Leu Asp Thr Gly Arg His Met
                130                 135                 140
    Pro Gly Ala Gly Lys Arg Arg Glu Lys Gly Asp Gly Val Tyr Gln Lys
    145                 150                 155                 160
    Gly Met Asp Phe Ile Leu Glu Lys Leu Asn His Gly Asp Trp Val His
                    165                 170                 175
    Ile Phe Pro Glu Gly Lys Val Asn Met Ser Ser Glu Phe Leu Arg Phe
                    180                 185                 190
    Lys Trp Gly Ile Gly Arg Leu Ile Ala Glu Cys His Leu Asn Pro Ile
                    195                 200                 205
    Ile Leu Pro Leu Trp His Val Gly Met Asn Asp Val Leu Pro Asn Ser
                210                 215                 220
    Pro Pro Tyr Phe Pro Arg Phe Gly Gln Lys Ile Thr Val Leu Ile Gly
    225                 230                 235                 240
    Lys Pro Phe Ser Ala Leu Pro Val Leu Glu Arg Leu Arg Ala Glu Asn
                    245                 250                 255
    Lys Ser Ala Val Glu Met Arg Lys Ala Leu Thr Asp Phe Ile Gln Glu
                    260                 265                 270
    Glu Phe Gln His Leu Lys Thr Gln Ala Glu Gln Leu His Asn His Leu
                    275                 280                 285
    Gln Pro Gly Arg Val Glu Ser Gly Gly Gly Ser Pro Gly Ala Pro
                290                 295                 300
    Trp His Leu Ser Ser Gln Tyr Ser Arg Thr Gly Ser Gly Cys
    305                 310                 315

<210> SEQ ID NO 14
<211> LENGTH: 9
<212> TYPE: PRT
<213> ORGANISM: Artificial Sequence
<220> FEATURE:
<223> OTHER INFORMATION: Polylinker peptide

<400> SEQUENCE: 14

Val Glu Glu Ser Gly Gly Gly Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Polylinker peptide

<400> SEQUENCE: 15

Val Glu Ser Gly Gly Gly Gly Ser Pro Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Polylinker peptide

<400> SEQUENCE: 16

Leu Glu Ser Gly Gly Gly Gly Ser Pro Gly
1               5                   10
```

```
<210> SEQ ID NO 17
<211> LENGTH: 9
<212> TYPE: PRT
<213> ORGANISM: Artificial Sequence
<220> FEATURE:
<223> OTHER INFORMATION: Polylinker peptide

<400> SEQUENCE: 17

Leu Glu Glu Ser Gly Gly Gly Gly Ser
1               5
```